(12) United States Patent
Pribenszky et al.

(10) Patent No.: US 8,415,093 B2
(45) Date of Patent: *Apr. 9, 2013

(54) POST-THAW SURVIVAL OF CRYOPRESERVED BIOLOGICAL MATERIAL BY HYDROSTATIC PRESSURE CHALLENGE

(75) Inventors: Csaba Pribenszky, Székesfehérvár (HU); Miklós Molnár, Budapest (HU)

(73) Assignee: Cryo-Innovation Kft., Szeged (HU)

( * ) Notice: Subject to any disclaimer, the term of this patent is extended or adjusted under 35 U.S.C. 154(b) by 0 days.

This patent is subject to a terminal disclaimer.

(21) Appl. No.: 13/016,512

(22) Filed: Jan. 28, 2011

(65) Prior Publication Data

US 2011/0189648 A1 Aug. 4, 2011

Related U.S. Application Data

(63) Continuation-in-part of application No. 10/571,236, filed as application No. PCT/IB2004/051711 on Sep. 8, 2004, now Pat. No. 7,879,539.

(30) Foreign Application Priority Data

Sep. 9, 2003 (HU) ..... 0302888
Dec. 31, 2003 (HU) ..... 0304124

(51) Int. Cl.
*A01N 1/00* (2006.01)
(52) U.S. Cl.
USPC ......... 435/1.1
(58) Field of Classification Search ........... None
See application file for complete search history.

(56) References Cited

U.S. PATENT DOCUMENTS 4,559,298 A * 12/1985 Fahy ............ 435/1.2
7,879,539 B2 2/2011 Pribenszky et al.

OTHER PUBLICATIONS

Abe, F., and Horikoshi, K. (1995). *Hydrostatic Pressure Promotes the Acidification of Vasuoloes in Saccharomyces Cerevisiae*. FEMS Microbiol Lett 130, 307-312.
Abe, F., and Horikoshi, K. (1997). *Vacuolar acidification in Saccharomyces Cervisiae induced by elevations hydrostatic pressure is transient and is medicated by vacuoloar H+-ATPase*. Extremophiles 1, 89-93.
Abe, F., and Horikoshi, K. (1998). *Anyalysis of Intracellular pH in the Yeast Saccharomyces Cerevisiae Under Elevation Hydrostatic Pressure: A Study in Baro-Physiology*. Extremophiles. 2, 223-228.
Abe, F., Kato, C. and Horikoshi, K. (1999). *Pressure-regulation metabolism in microorganisms*. Trends Microbiol 7, 447-453.
Aldridge, RE., Bruner, L.J. (1985). *Pressure effects on mechanisms of charge transport across bilayer membranes*. Biochim Biophys Acta 817,343-354.
Archer, J., Gook, D.A., Edgar, D.H. (2003). *Blastocyst formation and cell numbers in human frozen-thawed embryos following extended culture*. Human Reproduction (Oxford, England) 18, 1669-1673.
Baguisi, A. Arav, A, Crosby, T.F., Roche, J.F., and Boland, M.P. (1997). *Hypothermic storage of sheep embryos with antifreeze proteins: development in vitro and in vivo*. Theriogeneology 48, 1017-1024.
Bridgman P.W. (1911). *Water in the liquid and five solid forms under pressure*. Proceedings of the American Academy of Arts and Science 47,441-558.
Butz P., Ludwig H. (1986). *Pressure inactivation of microorganisms at moderate temperatures*. Physica B+C 139-140,875-877.
Fahy, G.M., MacFarane, D.R., Angell, C.A. and Meryman, H.T. (1984). *Vitrification as an approach to cryopreservation*. Cryobiology 21. 407-426.
Fukuda, A., Osawa, T., Oda, H., Tanaka, T., Toyokuni, S. and Uchida, K. *Oxidative stress response in iron induced acute nephrotoxicity: enhanced expression of heat shock protein 90*. Biochem Biophys Res Commun 1996; 219:76-81.
Garcia-Gardena, G., Fan, R., Shah, V., Sorrentino, R.. Cirino, G., Papapetropoulos. *Dynamic activation of endothelialnitric oxide synthase by HSP90*. Nature 1998; 392: 821-4.
Graumann, P.L., Marahiel M.A. (1999). *Cold shock proteins CspB and CspC are major stationary-phase-induced proteins in Bacillus subtilis*. Arch Microbial 171, 135-138.
Gross, M., Jaenicke, R. (1994). *Proteins under pressure. The influence of high hydrostatic pressure on structure, function and assembly of proteins and protein complexes*. Eur J Biochem 221,617-630.
Huang, S.Y, Kuo, YH., Lee, W.C., Tsou, H.L., Lee, YP., Chang, H.L. et al. *Substantial decrease of heat-shock protein 90 precedes the decline of sperm motility during cooling of boar spermatozoa*. Theriogenoloy 1999; 51:1007-16.
Huang, S.Y, Kuo, Y.H., Tsou, H.L., Lee, W.C.,King, Y.T., Huang, H.C. et al. *The decline of porcine sperm motility by geldanamycin, a specific inhibitor of heat shock protein 90 (HSP90)*, Theriogenology 2000; 53: 1117-84.
Ishwar, A.K., Memon, M.A. (1996). *Embryo transfer in sheep and goats: a review*. Small Ruminant Research 19, 35-43.
Jaenicke, R. (1991). *Protein stability and molecular adaptation to extreme conditions*. Eur J Biochem 202, 715-728.
LaTena, A., Brandi, A., Falconi, M., Spurio, R., Pon, C.L., Gualerzi, C.O. (1991). *Identification of a cold-shock transcriptional enhancer of the Escherichia coli major cold shock gene encoding nucleotide protein H-NS*. Proc Natl Acad Sci USA 88, 10907-10911.
Leibo, S.P. and Songsasen, N. (2002). *Cryopreservation of garnets and embryos of non-domestic species*. Theriogenology 57. 303-326.
Medeiros, C.M.O., Forell, F., Oliveira, A.T.D., and Rodrigues, J.L. (2002). *Current Status of Sperm Cryopreservation: Why Isn't It Better?* Theriogenology 57:327-344.
Murakami, T.H., Zimmerman, A.M. (1973). *DNA syntheseis in Tetrahymena: a pressure study*. Cytobios 7,171-181.
Nowshari, M.A., Brem, G. (1998). *Effect of cryoprotectants and their concentration on post-thaw survival and development of expanded mouse blastocysts frozen by a simple rapid freezing procedure*. Theriogenoloy 50, 1001-1013.

(Continued)

*Primary Examiner* — Sandra Saucier
(74) *Attorney, Agent, or Firm* — Jason D. Voight

(57) ABSTRACT

The present invention relates to a method for improving post-thaw survival of cryopreserved biological material comprising applying hydrostatic pressure to said biological material; keeping the said biological material at the hydrostatic pressure for a predetermined time period; releasing the hydrostatic pressure; and freezing the said biological material using any protocol applicable thereto.

18 Claims, 3 Drawing Sheets

OTHER PUBLICATIONS

Palou, E., Lopez-Malo, A., Barbosa-Canovas, G.V., Welti-Chanes, I., and Swanson, B.G. (1997). *Kinetic analysis of Zygosaccharomyces bailii inactivation by high hydrostatic pressure*. Lebensm.-Wiss. U. Technol. 30, 703-708.

Pearl, L.H.and Prodromou, C. *Structure and in vivo function of Hsp 90*. Curro Opin Struct Biol 2000; 10:46-51.

Pequeux, A., and Gilles, R. (1978). *Effects of high hydrostatic pressures on the activity of the membrane A TPases of some organs implicated in hydro mineral regulation*. Comp Biochem Physiol B Biochem Mol Biol 59, 207-212.

Phadtare, S., Alasina, J., Inouye, M. (1999). *Cold-shock response and cold-shock proteins*. CUff Opin Microbiol 2, 175-180.

Prodromou, C., Roe, S.M., O'Brian, R., Ladbury, J.E., Piper, P.W. amd Pearl, L.H. *Identification and structural characterization of the ATP/ADP-binding site in the HSP90 molecular chaperone*. Cell 1997; 90:65-75.

Rall, W.F. and Fahy, G.M. (1985). *Ice-free cryopreservation of mouse embryos at—196° C. by vitrification*. Nature 313, 573-575.

Reubinoff, B.E., Pera, M.E., Vajta, G., and Trounson, A.O. (2001). *Effective cryopreservation of human embryonic stem cells by the open pulled straw vitrification method*. Human Reproduction 16, 2187-2194.

Routray, P., Suzuki, T., Striissmann, C.A. and Takai, R. (2002). *Factors affecting the uptake of DMSO by the eggs and embryos of medaka, Oryzias latipes*, Theriogenology 58. 1483-1496.

Schmid, G., Liidemann, H. D., and Jaenicke, R. (1975) *High pressure effects on the activity of glycolytic enzymes*. Biophys Chern 3, 90-98.

Schuster, B., Sleytr, D.B. (2002). *The effect of hydrostatic pressure on S-layer-supported lipid membranes*. Biochim Biophys Acta 1563, 29-34.

Seki, K., Toyoshima, M. (1998). *Preserving tardigrades under pressure*. Nature 395, 853854.

Silva, J.L., Foguel, D., Royer, C.A. (2001). *Pressure provides new insights into protein folding, dynamics and structure*. Trends Biochem Sci 26, 612-618.

Spilimbergo, S., Elvassore, N., Bertucco, A. (2002). *Microbial inactivation by high-pressure*. The Journal of Super critical Fluids 22, 55-63.

Stachecki, J.J., Cohen, J., Schimmel, T., Willadsen, S.M. (2002). *Fetal development of mouse oocytes and zygotes cryopreserved in a nonconventional freezing medium*. Cryobiology 44, 5-13.

Takahashi, T., Kakita, A., Takahashi, K., Yokoyama, I., Sakamoto, I., Yamashina, S. (2001). *Preservation of rat livers by supercooling under high pressure*. Transplantation Proceedings 33, 916-919.

Tinneberg, H.-R., Roberts, T.K., Cheng, C.Y. Mrettler, L. (1980). *High hydrostatic pressure as an improvement for sperm cryopreservation*. Archives of Andrology 5, 42-43.

Tuboly, E., Lebovics, V.K., Gail, 6., Meszaros, L., Farkas, J. (2003). *Microbiological and lipid oxidation studies on mechanically deboned turkey meat treated by high hydrostatic pressure*. Journal of Food Engineering 56, 241-244.

Van Wagtendonk-De Leeuw, A.M., Den Daas, J.H., Kruip, T.A., Rall, W.F. (1995). *Comparison of the efficacy of conventional slow freezing and rapid cryopreservation methods for bovine embryos*. Cryobiology 32, 157-167.

Van Wagtendonk-De Leeuw, A.M., Den Haas, J.H.G., and Rall, W.F. 1997. *Field trial to compare pregnancy rates of bovine embryo cryopreservation methods: vitrification and one step dilution versus slow freezing and three-step dilution*. Theriogenology 48, 1071-1084.

Watson, P.F. *The effect of cold shock on sperm cell membranes*. In: Morris, GJ. and Clarke, A. eds. *Effects of low temperature on biological membranes*. London: Academic Press; 1981. p. 189-218.

Weber, G., Drickamer, H.G. (1983). *The effect of high pressure upon proteins and other biomolecules*. Q Rev Biophys 16, 89-112.

Welch, T.J., Farewell, A., Neidhardt, F.C., Bartlett, D.H. (1993). *Stress response of Escherichia coli to elevated hydrostatic pressure*. J Bacteriol175, 7170-7177.

Wemekamp-Kamphuis, H.H., Karatzas, AX., Wouters, J.A., Abee, T. (2002). *Enhanced levels of cold shock proteins in Listeria monocytogenes L028 upon exposure to low temperature and high hydrostatic pressure*. Appl Environ Microbiol 68, 456-63.

Wen-Lei Cao et al. *Cryopreservation-induced decrease in heat-shock protein 90 in human spermatozoa and its mechanism*. Asian J Andro12003; 5:43-46.

Wouters, J.A., Jeynov, B., Rombouts, F.M., de Vos, W.M., Kuipers, O.P., Abee, T. (1999). *Analysis of the role of 7 kDa cold-shock proteins of Lactobacillus lactis MG 1363 in cryoprotection*. Microbiology 145, 3185-3194.

Yager, P., Chang, E.L. (1983). *Destabilization of a lipid non-bilayer phase by high pressure*. Biochim Biophys Acta 731, 491-494.

Yamanaka, K., Fang, L., Inouye, M. (1998). *The CspA family in Escherichia coli: multiple gene duplication for stress adaptation*. Mol Microbiol27, 247-255.

Arii et al., "Cryoprotection of Medaka embryos during development", Zoological Science 4 (5) : 813-818 (1987).

Pribenszky et al., "Stress for stress tolerance? A fundamentally new approach in mammalian embryology", Biol Reprod; Jun. 10, 2010, vol. 83, pp. 690-697.

* cited by examiner

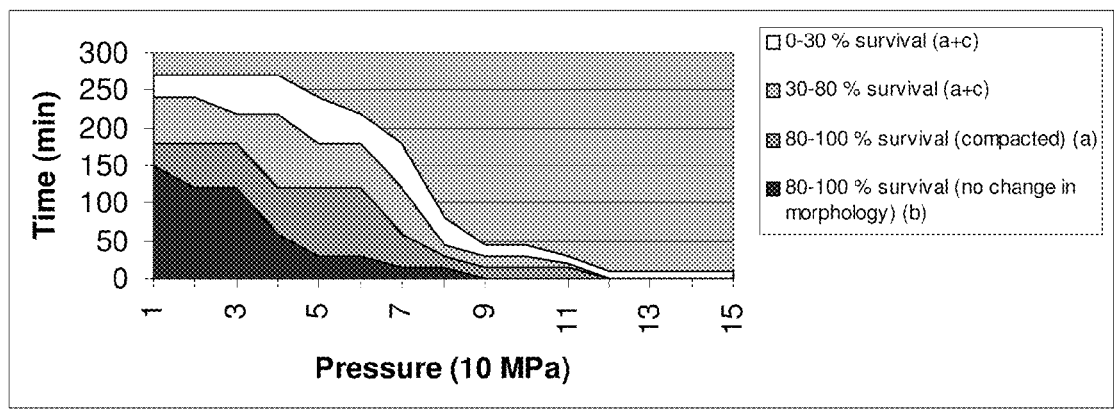
Figure 1.
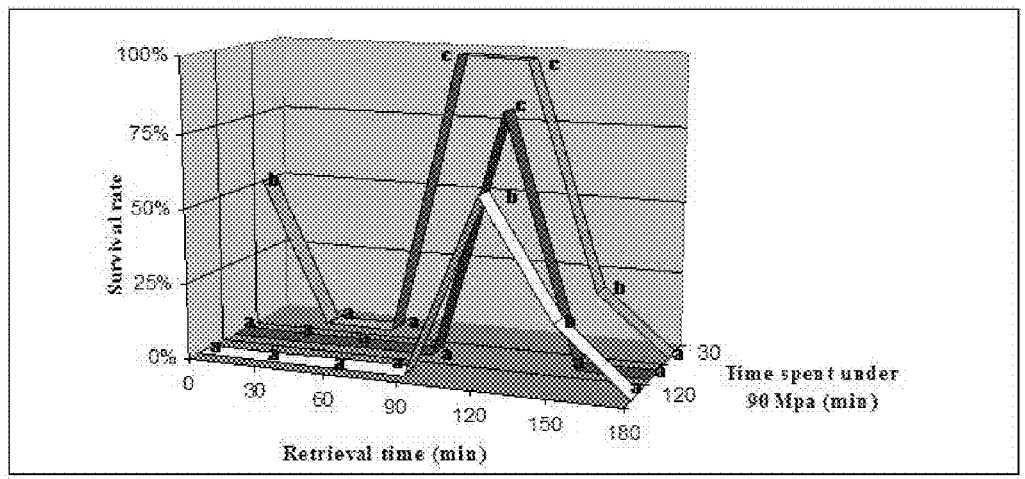
Figure 2.
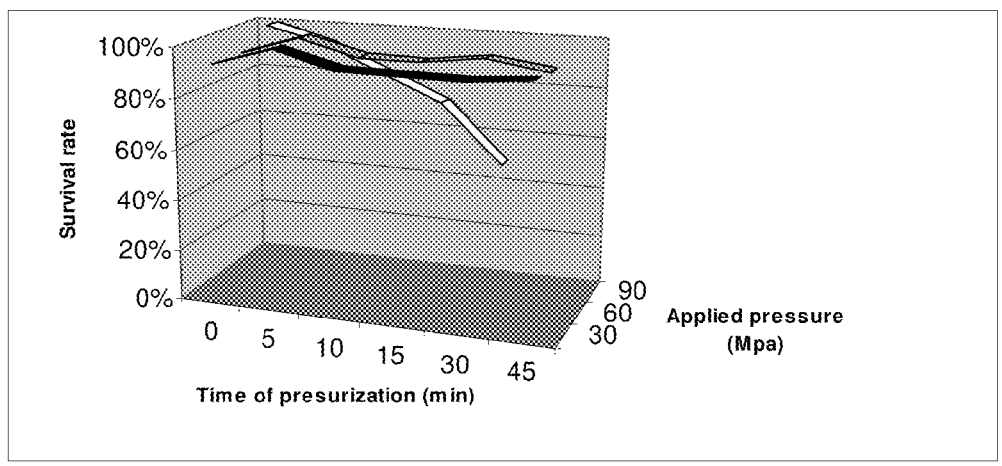
Figure 3.a

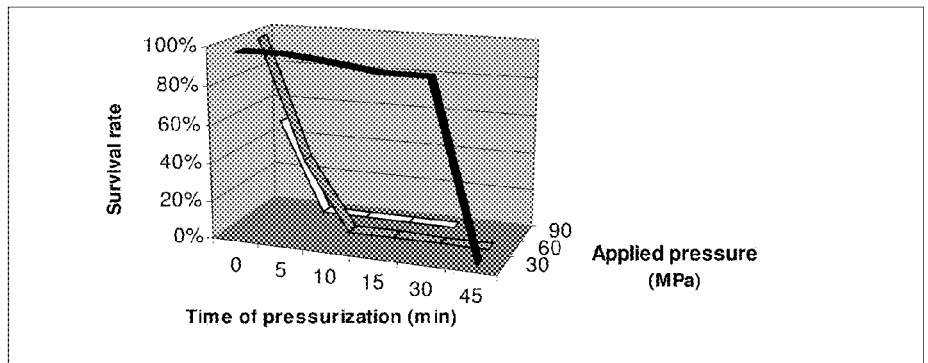
Figure 3.b
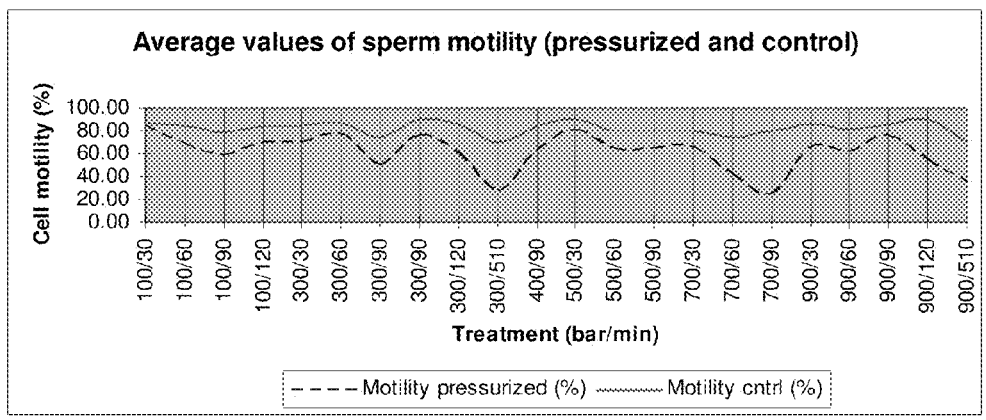
Figure 4
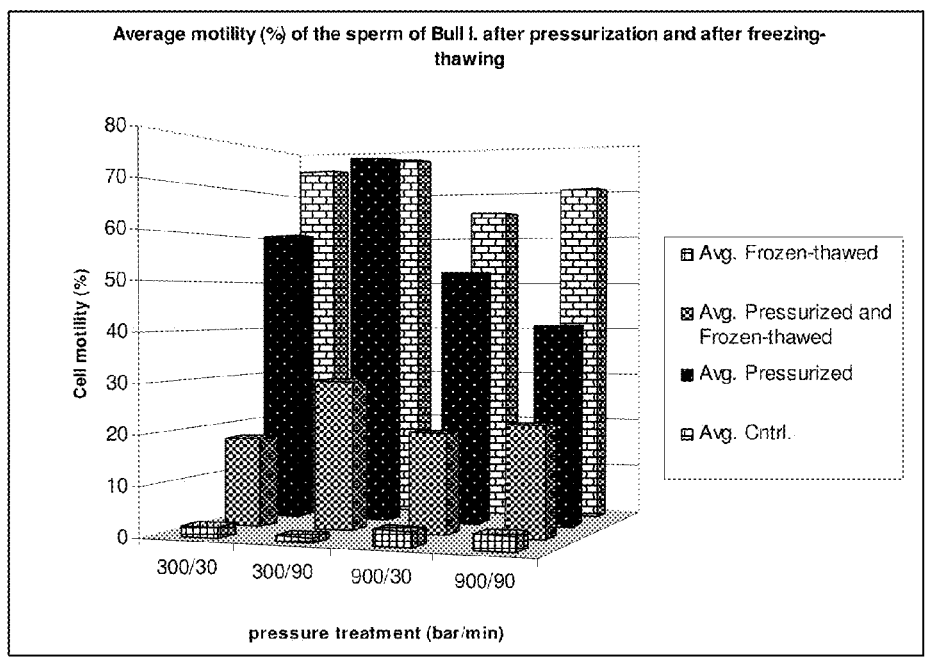
Figure 5

POST-THAW SURVIVAL OF CRYOPRESERVED BIOLOGICAL MATERIAL BY HYDROSTATIC PRESSURE CHALLENGE

This is a continuation-in-part of application Ser. No. 10/571,236, filed Dec. 15, 2006, now U.S. Pat. No. 7,879,539 which is the national phase of international application PCT/IB04/51711, filed Sep. 8, 2004, the entire disclosure of which is hereby incorporated by reference herein.

The present invention relates to a method for improving post-thaw survival of cryopreserved biological material comprising applying hydrostatic pressure to said biological material; keeping the said biological material at the hydrostatic pressure for a predetermined time period; releasing the hydrostatic pressure; and freezing the said biological material using any protocol applicable thereto.

The process of cryopreservation is well established to store biological material for a wide variety of purposes in different fields of modern biology and biotechnology. These methods follow very similar basic steps:

1. Treatment of the biological material with a solution containing cryoprotective agents.
2. The next step comprises freezing of the biological material to subzero temperature.
3. The so prepared biological material is stored—even for very long time periods—at low temperature, for example in liquid nitrogen.
4. Prior to use the biological material is warmed back.
5. The cryoprotective agents may be removed from the biological material. In addition, the biological material may require further steps to restore its original viability.

Several approaches has been tried to improve this above-outlined basic protocol, since the process of cryopreservation is harmful to biological material. Approaches to avoid ice formation through the ultra-rapid cooling and warming rates or by gradual depression of the equilibrium freezing point during cooling to −80° C. have not given a proper solution for every field of cryobiology. Attempts were made to improve survival after freezing: at vitrification highly concentrated aqueous solutions of cryoprotective agents supercool to very low temperatures, allowing intracellular vitrification (Rall and Fahy, 1985). Though Fahy et al. (1984) mentioned the possible use of considerably increased hydrostatic pressure as an additional factor that may facilitate vitrification, but also considered that it had few practical consequences in reproductive biology. Other studies report the use of antifreeze proteins (AFPs) which non-colligatively lower the freezing point of aqueous solutions, block membrane ion channels and thereby confer a degree of protection during cooling (Baguisi et al., 1987). The toxic effects of the cryoprotectants and the harmful consequences of the osmotic changes are not negligible at any of the described methods.

These procedures, at present, have a varying degree of efficiency for various applications. For example, in case of preserving embryos, the efficiency of cryopreservation ranges from 0 to 80 percent, depending on the species, freezing method, embryonic stage of development (Ishwar, 1996; Van Wagtendonk-De Leeuw, 1995, 1997; Medeiro, 2002; Reubinoff, 2001; Hammitta, 2003; Archer, 2003; Stachecki, 2002, Leibo and Songsasen, 2002). The success rates for the cryopreservation of human ova, being currently a popular issue, are also far from being satisfactory.

Since 1912 it has been known that water undergoes different phases when submitted to hydrostatic pressure at different temperatures (Bridgman, 1911). Solutions can be maintained unfrozen even at low subzero temperatures by applying a certain pressure to them (Bridgeman, 1970). High hydrostatic pressure (HHP) was previously used by Takahashi et al. (2000, 2001) at subzero preservation of rat livers for transplantation in order to reduce cryoinjuries. This approach uses HHP to reduce substantially the freezing point of the culture medium, thus preserving the biological material at subzero temperature without any of the negative effects of cryopreservation. This approach was found unreliable by the present inventors in preserving mouse embryos, as outlined below in examples 2 and 3.

A recent study by Routray et al. (2002) showed that hydrostatic pressure (5 MPa) facilitated the uptake of DMSO in the experiment conducted with eggs and embryos of medaka (*Oryzias latipes*), though there was a rapid loss in the viability.

Hydrostatic pressure in the range of 30-50 MPa usually inhibits the growth of various organisms: the initiation of DNA replication is one of the most pressure-sensitive intracellular processes (Abe et al., 1999). The effects vary in severity depending upon the magnitude and duration of compression (Murakami and Zimmerman, 1973). The cell membrane is noted as a primary site of pressure damage (Palou et al., 1997). High hydrostatic pressure treatment can alter the membrane functionality such as active transport or passive permeability and therefore perturb the physico-chemical balance of the cell (Yager and Chang, 1983; Aldridge and Bruner, 1985; Macdonald, 1987; Schuster and Sleytr, 2002). The physical or biochemical processes at altered pressure conditions are governed by the principle of Le Chatelier: all reactions that are accompanied by a volume decrease speed up considerably (Murakami and Zimmerman, 1973; Welch et al., 1993; Palou et al., 1997). The application of pressure can lead to a population of conformers of proteins, including partially or completely unfolded conformations. Pressure can cause the denaturation of proteins by the combined effects of breakage of intraprotein interactions and release of cavities followed by the binding of water (Schmid at al., 1975; Weber and Drickamer, 1983; Jaenicke, 1991; Gross and Jaenicke, 1994; Silva et al., 2001).

Recent reports state that hydrostatic pressure enhances the production of shock proteins (Welch et al., 1993; Wemekamp-Kamphuis et al., 2002). Studies describe that instabilities caused by sublethal cold shock in the normal protein synthesis in bacteria are overcome by the synthesis of so-called cold-shock proteins (CSPs, HSPs) (Phadtare et al., 1999). CSPs, HSPs are suspected to have many functions such as RNA chaperones (Graumann and Marahiel, 1999) or transcription activators (LaTena et al., 1991); it was assumed that they also play a role in the protection against freezing (Wouters et al., 1999). Further investigations found that the production of CSPs and HSPs are not only induced by cold shock, but by other environmental stresses also. In *E. coli*, for example, a type of CSP is produced by nutritional stress (Yamanaka et al., 1998). Another trial showed that high hydrostatic pressure treatment provoked the production of certain cold-induced proteins and heat shock proteins (Welch et al., 1993). Other recent reports state that hydrostatic pressure enhances the production of shock proteins (Wemekamp-Kamphuis, et al., 2002). Since cold-shock and high pressure-treatment both increases CSP and HSP levels, trials were conducted about the possibility of cross-protection. Wemekamp-Kamphuis et al. (2002) found that the level of survival after pressurization of cold-shocked *Listeria monocytogenes* was 100-fold higher than that of the cells growing at 37° C.

While food-microbiologists study the above-mentioned processes in order to kill detrimental microorganisms (Butz and Ludwig, 1986; Wemekamp-Kamphuis et al., 2002; Spilimbergo et al., 2002), the aim of the present invention is to enhance the survival of cryopreserved biological material.

More attention is paid recently to study the role of shock proteins in cryopreservation. Huang et al. (1999) published that a substantial decrease of a shock protein, HSP90, might be associated with a decline in sperm motility during cooling of boar spermatozoa. Wen-Lei Cao et al. (2003) reported that HSP90 in human spermatozoa was decreased substantially after cryopreservation that may result from protein degradation.

As a summary, HSP90, which is induced by high hydrostatic pressure is:
Cytosolic protein
Molecular chaperone, plays an essential role in stress tolerance, protein folding, signal transduction, etc.
  Has been shown to possess an inherent ATPase that is essential for the activation of authentic client proteins in vivo (Pearl and Prodromou, 2000).
  Associated with semen motility:
    Activate nitric oxide synthetase (NOS) (Garcia-Gardena et al., 1998)
    Protect cells from reactive oxygen species (ROS) (Fukuda et al., 1996), which increase significantly during the cooling process and impair greatly sperm motility
    Involved in ATP metabolism (Prodromou et al., 1997). ATP level is diminished after cold shock, and would not restore later (Watson, 1981)
  HSP 90 decreased substantially together with the decline of sperm motility after cooling boar semen. It was concluded, that HSP 90 might play a crucial role in regulating porcine sperm motility (Huang et al., 1999)
  Geldanamycin, a specific HSP 90 inhibitor, significantly reduced the sperm motility of boar semen in a dose- and time dependant manner (Huang et al., 2000).

HSP90 decreased substantially after cryopreservation in human spermatozoa, together with the sperm motility; the decrease was not due to leaking, but a result of protein degradation (Wen-Lei C A O et al., 2003).

The accumulation of the pressure effects is lethal beyond a certain level: while irreversible changes of some biomolecules take place at higher pressures, at 300 MPa most bacteria and multicellular organisms die. Though tardigrades—in their active state they die between 100 to 200 MPa—can survive up to 600 MPa if they are in a dehydrated 'tun' state (Seki and Toyoshima, 1998).

As can be seen from the above, in vitro culture, storage, and manipulation of gametes and embryos require meticulously adjusted conditions to avoid or minimize the harmful effects of uncontrolled stress. However, the present inventors surprisingly found that a well-defined and properly applied stress may induce general adaptation and increase tolerance to various in vitro procedures, including cryopreservation. Treatment with sublethal doses of HHP resulted in increased morphological survival, fertilizing ability, or developmental potential after various in vitro or in vivo procedures. HHP treatment of spermatozoa, oocytes, embryos, and embryonic stem cells increased fertilizing ability, developmental competence, and differentiation and improved results after cryopreservation, parthenogenetic activation, intracytoplasmic sperm injection, and somatic cell nuclear transfer. Osmotic stress of oocytes resulted in higher developmental rates after cryopreservation, parthenogenetic activation, and somatic cell nuclear transfer. Although cellular and subcellular mechanisms supposedly contributing to these processes require further research, the new principle, i.e., to improve the stress tolerance by a defined HHP sublethal stress, outlines a completely new strategy in mammalian embryology, as well as cryopreservation of other cells and tissues, with remarkable theoretical and practical consequences.

The present invention discloses that by applying a hydrostatic pressure challenge, and then by following state of the art cryopreservation protocols, the survival of biological material can be improved significantly. In the context of the present invention, the term survival means, inter alia, improved continued in vitro and in vivo development, higher hatching or implantation and birth rates (in case of embryos); higher post thaw motility and/or improved capacity for fertilization (in case of sperm); improved continued in vitro and in vivo development, improved capacity for being fertilized, higher hatching or implantation and birth rates (in case of oocytes), higher rate of retained normal function and/or differentiation (in case of stem cells). It is appreciated that the term survival may encompass different other functional characteristics depending on the type of other biological material treated.

For this purpose the pressure tolerance of certain types of biological materials was established (see example 1), followed by the investigation of several state of the art concepts to achieve the aim of improving the survival of pressurized biological material (see examples 2 and 3). Then the present inventors further investigated the effects of pressure treatment on different types of biological material and unexpectedly found the inventive method of pressure challenge to fulfill their objectives.

In this context we must emphasize that the present inventive concept equally applies to many different cryopreservation protocols, and the choice of those is not limited with respect to the invention. The only necessary step to include in the improved protocols is the step of hydrostatic pressure challenge; the parameters of which can be easily optimized by a person skilled in the art when following the teachings of the present description.

SUMMARY OF THE INVENTION

The present invention relates to a method for improving post-thaw survival of cryopreserved biological material comprising
(a) applying hydrostatic pressure to said biological material, optionally according to a predetermined pressure-time profile;
(b) keeping the said biological material at the hydrostatic pressure for a predetermined time period;
(c) releasing the hydrostatic pressure;
(d) freezing the said biological material using any protocol applicable thereto.

In an embodiment, pressure used in the method according to the invention is in the range of 1 to 250 MPa. In preferred embodiments, the pressure is preferably in the range of 10 to 100 MPa, more preferably 20 to 75 MPa, and still more preferably 30 to 60 MPa.

In another embodiment, the hydrostatic pressure used in the method according to the invention is applied for a time period between 1 second and 300 minutes. In preferred embodiments, the pressure is applied preferably for a time period between 1 second and 150 minutes, more preferably between 1 second and 90 minutes, and still more preferably between 1 second and 60 minutes.

In other embodiments, the method according to the invention comprises the gradual release of the pressure over a time period between 1 second and 4 hours. In other embodiments the time period for releasing the pressure is between 10 second and 2 hours, or between 1 minute and 1 hour, or in other cases between 10 min and 30 min. The release of pressure can be instantaneous.

In a preferred embodiment the method according to the invention is used in connection with biological material selected from the group consisting of oocytes, sperms, zygotes, morulas, blastocysts, embryos, stem cells, cells or tissues of a vertebrate animal.

Other preferred embodiments relate to a method wherein the said vertebrate animal is a fish, bird or a mammal, preferably bovine, equine, caprine, ovine, swine, other livestocks, pets, primates, including human.

In preferred embodiments, the use of the invention involves a pressurizing device, which includes a pressure chamber suitable for receiving the biological material, and means to provide controlled pressure in the range of 1 to 250 MPa preferably 10 to 100 MPa, more preferably 20 to 75 MPa, and still more preferably 30 to 60 MPa.

In other preferred embodiments, the use of the invention involves a pressurizing device, which comprises means to maintain the said pressure for a time period between 1 second and 300 minutes, preferably between 1 second and 150 minutes, more preferably between 1 second and 90 minutes, and still more preferably between 1 second and 60 minutes.

In a preferred embodiment the use of the invention encompasses the use of a control system in connection with the pressurizing device for controlling the depressurization of the pressure chamber over a time period between 1 second and 4 hours.

DETAILED DESCRIPTION

For the sublethal stressor, HHP treatment is chosen due to its unique and outstanding features: 1) acts instantly and uniformly at every point of the sample, 2) HHP features zero penetration problems or gradient effects, 3) HHP can be applied with the highest precision, consistency, reliability, and safety.

Experiments followed a common scheme. First, samples (spermatozoa, oocytes, embryos, or embryonic stem cells) are exposed to different levels (5-80 MPa) of hydrostatic pressure applied for various times in the range of 10-120 min to determine the sublethal zone.

In the context of the present invention, the term "sublethal" means the type of treatment that does not cause loss in cell's survival. In other words, the treatment that is not sufficient to cause death. The limit of the lethal treatment in this context is when treatment begins to cause significant losses in cell survival ($p=0.05$). If the treatment does not reach this level, but conveys at least 10% intensity of the treatment that caused significant losses ($p=0.05$), then the treatment was sublethal.

Generally, for HHP treatment, oocytes, embryos, spermatozoa, embryoid bodies, or other cells or tissues are loaded into suitable containers (e.g., 0.25- or 0.5-ml ministraw, 5-ml maxistraw, 100- to 500-ml transfusion bag) in conventional culture or extender media (e.g., TCM-199, M2, or G-MOPS for oocytes and embryos) and sealed hermetically, without air bubbles. Subsequently, containers are placed into the pressure chamber (filled with a liquid, for example distilled water) of the pressurizing device that was previously heated up to the required temperature (e.g., body or room temperature). The pressure chamber is closed, and the machine executes the pressure program according to the set parameters (magnitude and duration of the pressure, treatment temperature, pressure profile).

At the second phase of experiments, samples are exposed to this sublethal dose, then incubated for 5-120 min under normal culture conditions for recovery. Subsequently, the required intervention (cryopreservation, insemination, parthenogenetic activation, in vitro fertilization, in vitro maturation or culture, or enucleation followed by somatic cell nuclear transfer) is performed. Results are assessed by investigating morphology as well as functional parameters, including motility, membrane integrity, fertilizing ability, and developmental competence. In each experiment, treatment groups are compared with a single control group where HHP treatment was omitted.

Surprisingly, the pressure tolerance limit of mammalian gametes and embryos was found in the 20-80 MPa zone, where cells survived 30- to 120-min treatments without any loss of their viability, although the highest hydrostatic pressure that these cells normally encounter is less than 0.2 MPa. The optimal and sublethal pressure ranges for gametes and embryos of different mammalian species are shown in Table 1.

The present invention is described in more detail by using porcine, mouse or human eggs, mouse embryos and mouse embryonic stem cells, for the purpose of demonstrating the inventive concept. It should be apparent that the disclosed procedures equally apply to all kind of different biological materials which are routinely cryopreserved in the art. It is obvious, however, that the results of the present invention are unexpected and/or advantageous, and such results, based on the diverse distribution of examples presented herein, are likely to be exhibited over a wide range of biological material.

It is needless to say that the cryopreservation of embryos, oocytes and stem cells are in the forefront of the cryopreservation research due to its industrial and healthcare applicability. However, in the method according to the invention and similarly in the present description, either one of the terms "mouse embryo" or "oocyte" can be used interchangeably with the term "biological material". In the present specification, experimental data are also presented for partenotes and IVF embryos generated from oocytes by ICSI (intracitoplasmic sperm injection) and embryonic stem cells providing unexpectedly enhanced post-thaw survival. Exemplary biological material can be, for example, pre- and postimplantation stages of embryos of different mammalian species, oocyte, sperm, stem cells, tissues, organs of vertebrate animals and human, or even the entire body. The vertebrate animal can be of any species, for example a fish, bird or a mammal, preferably bovine, equine, caprine, ovine, swine, other livestocks, pets, primates, including human.

As highly developed eukaryotic organisms, embryos and oocytes are more susceptible to the effect of hydrostatic pressure than tardigrades and bacteria. The first objective therefore is to establish the basic features of embryos and oocytes under pressure concerning their morphology and survival.

Carefully designed experiments were conducted to investigate the pressure tolerance of different biological materials. The choice of pressure and time scale used was defined to give the widest applicable range for later practical applications. More particularly, the hydrostatic pressure that can be applied is 0.2, 1, 5, 10, 15, 20, 25, 30, 40, 50, 60, 70, 80, 90, 100, 110, 120, 130, 140, 150, 200 or 250 MPa, or any value in between these intermediate ranges.

The hydrostatic pressure can be applied to said biological material according to a predetermined pressure-time profile. It will be appreciated by the person skilled in the art that, depending on the biological material to be treated, the pressure applied to the material may be increased gradually over time. The profile appropriate for a given biological material can be determined empirically, and it may be linear, stepwise, or other conventionally used time profile.

Similarly, a wide period of time can be selected for the biological material to be kept under high hydrostatic pressure. More particularly, the mouse embryos are kept under the selected pressure for a time period between 1 second and 6 hours, more specifically 1 s, 5 s, 10 s, 20 s, 30 s, 40 s, 50 s, 1 min, 2 min, 3 min, 4 min, 5 min, 6 min, 8 min, 10 min, 15 min, 20 min, 30 min, 40 min, 50 min, 60 min, 70 min, 80 min, 90 min, 120 min, 150 min, 180 min, 210 min, 240 min, 300 min or 360 min. The time the embryos survive under pressure reduces with increasing pressure.

It is appreciated by the person skilled in the art that the time between the end of the pressure pre-treatment and the beginning of the cryopreservation can be considerably different in specific embodiments. Depending the given protocol, the state of the biological material may change in this time frame. This period may allow for the physical recovery of the cells if long enough or, conversely, cellular processes may commence, i.e. the synthesis and accumulation of shock proteins could take place. In different circumstances these effects may prove either beneficial or damaging; therefore optimization of the protocol may be necessary in this regard through experimentation.

FIG. 1 shows that embryos can survive a substantial amount of pressure without any visible change in their morphology (e.g., 90 MPa for 1 s or 30 MPa for 2 h). The embryos compacted depending on the magnitude and the duration of the applied pressure treatment. Without limiting the scope of the invention by theory, we assume that pressure can not be directly responsible for squeezing the water out of the blastocysts. Based on the cited documents, the compaction of the embryos was due to the consequences of pressure induced production of different proteins (cold-shock proteins, CSPs), reversible alterations in protein structure and metabolic processes. Compacted embryos could regain their normal morphology after 4-5 hours of in vitro culture, and resume development similarly to controls (e.g., embryos challenged by 90 MPa for 30 min or 30 MPa for 3 h).

Without limiting the scope of the invention by theory, it can be postulated from the studies with IVF bovine embryos that compaction is not a criterion for the optimal pressure pre-treatment. Compaction can be the result of pressure-altered membrane permeability, altered diffusion and active transport through the cell membranes. This reversible change in morphology can be considered as a morphological "sign" which marks that the embryo was treated with a "sub-lethal" impact. According to the literature, the "sub-lethal" shock is an impact that induces the production so-called "shock proteins", which are suspected to play role in the improvement of the success rate of cryopreservation.

However, in certain applications the compacted embryos can preferably be selected for cryopreservation. After pressurization, expanded blastocysts become compacted and stay in this form for 3-4 hours, then they re-expand. Based on this phenomenon, embryos treated with pressure before the freezing process can be selected. Since the morphological changes of the embryos and the beneficial effects of the pressure pre-treatment may come from the altered protein structure and/or features and/or the enhanced production of different pressure-induced proteins, the examination of these proteins can be indicative of the high hydrostatic pressure applied to the biological material before the cryopreservation process.

The pressure pre-treatment also correlates to a certain degree with the time when embryos regain their normal development after cryopreservation. Observing this process can indicate the nature of a pre-treatment, as using high hydrostatic pressure can considerably shorten the time necessary for regeneration.

The higher the magnitude of the pressure, the less time the embryos survive. Pressure impact exceeding a certain magnitude and duration caused irreversible changes: embryos became disintegrated after 2 hours of in vitro culture or were already disintegrated after decompression (e.g., embryos challenged by 90 MPa for 2 h or 30 MPa for 5 h). The person skilled in the art should be capable of determine these limit-pressures and limit-times by routine experimentation with respect to the specific biological material used.

It will be appreciated that the survival rate of the pressurized biological material can be enhanced by gradual decompression thereof. Studies showed that the survival rate of the pressurized embryos increased strikingly if they were retrieved gradually. While 60 minutes at 90 MPa was lethal for all of the embryos, 80% survived when 120 min. gradual decompression was used. The decompression time is also a feature of the present invention which is up to the person skilled in the art to determine in view of the specific application. More particularly, the biological material kept under the selected pressure are decompressed for a time period between 1 sec. and 4 hours, more specifically 1 s, 5 s, 10 s, 20 s, 30 s, 40 s, 50 s, 1 min, 2 min, 3 min, 4 min, 5 min, 6 min, 8 min, 10 min, 15 min, 20 min, 30 min, 40 min, 50 min, 60 min, 70 min, 80 min, 90 min, 120 min, 150 min, 180 min, 210 min or 240 min. Again, as with the application of the pressure, the decompression could be done according to a predetermined pressure-time profile.

Again, without being limited by theory, a possible explanation of this feature could be that a considerable amount of $CO_2$ is generated under pressure (Abe and Horikoshi 1995). The hydration and ionization of $CO_2$ ($HCO_3^-$ and $H^+$) are facilitated by elevated pressure because the reaction is accompanied by a decrease in volume (−0.26 ml/mol) in a manner dependent on the magnitude of the pressure applied (Palou at al. 1997, Welch at al. 1993). The intracellularly produced carbon dioxide instantly dissolves, and then dissociates to give $HCO_3^-$ and $H^+$, thus also reducing the intracellular pH (Abe and Horikoshi 1995, 1997, 1998, Abe et al. 1999). It can be assumed that the equilibrium maintained by elevated pressure is lethal for the embryos at atmospheric pressure. It may be also hypothesized that the instant decrease of pressure causes elevated release of $CO_2$ from its hydrated and ionized form from the cytoplasm, causing immediate death of the embryos. On condition of a certain decompression time, the plasma membrane proteins ($H^+$-ATPase) (Schmid et al. 1975, Péqueux and Gilles 1978) reversibly inactivated by elevated hydrostatic pressure, start to function again, (together with passive diffusion) shifting the equilibrium gradually towards the physiological state.

High hydrostatic pressure (HHP) was previously used by Takahashi et al. (2000, 2001) at subzero preservation of rat livers for transplantation in order to reduce cryoinjuries. This approach uses HHP to reduce substantially the freezing point of the culture medium, thus preserving the biological material at subzero temperature without any of the negative effects of cryopreservation. To investigate this method of cryopreservation in the case of mouse embryos, studies were designed to pressurize embryos at 0° C. The survival of the embryos reduced significantly. While at room temperature (RT) embryos had an average survival rate of 90% at 30 MPa for 45 min, none of the embryos survived the same impact at 0° C. After 10 minutes or 5 minutes at 0° C., 0% of the embryos survived at 60 MPa and at 90 MPa, respectively. In contrast, at room temperature, the survival rate was around 90% in both cases. Embryos were also pressurized at 0° C. and were decompressed gradually. The application of gradual decompression at low temperature did not have a beneficial effect on the embryo-survival. Based on these findings, the use of the phenomena is not applicable in this form, since pressure and low temperature together proved to be lethal for the embryos.

The present invention relates to the improvement post-thaw survival of cryopreserved mouse and bovine blastocysts, oocytes and stem cells by hydrostatic pressure challenge. This can be evaluated by observing continued in vitro development or differentiation, by partenogenetic activation and further in vitro culture, enucleation and somatic cell nuclear transfer followed by in vitro culture or by in vitro fertilization followed by in vitro culture, or by transferring the pressurized and/or otherwise generated embryos. In vitro development, implantation and further uterine development and birth of healthy pups are obvious proof of their biological and genetic potential.

As we disclosed in detail above, the survival rate of cryopreserved expanded mouse blastocysts could be improved by a certain pressure treatment before the freezing procedure. A pressure impact of 60 MPa for 30 min was applied to the blastocysts, where approximately 80% to 90% of the embryos became compacted and survival was not different from the untreated control. According to the results of the in vitro evaluation, the applied pressure treatment strikingly improves the in vitro development of the embryos after freezing. In vitro studies showed that the hydrostatic pressure challenge not only improves the survival rate of the blastocysts treated, but also improves the recovery time necessary to the embryos to regain their native state. In our exemplary studies, after 6 hours 98% of the pressure treated blastocysts were morphologically (diameter, structural integrity, and general morphology) exactly identical to the control embryos and 95% of the blastocysts fully hatched within 20 hours, together with the controls. Embryos frozen without pressure treatment reexpanded only 20 hours after thawing. The proportion of the re-expanded blastocysts was significantly inferior to those receiving pressure treatment (46% vs. 98%). In addition, no embryos hatched from this group. Therefore, it is clear that the method according to the invention is suitable to obtain highly viable mouse embryos for further implantation.

According to the results of in vitro evaluation of oocytes, the applied pressure treatment strikingly improves the in vitro survival and developmental capacity of the oocytes after freezing.

Porcine oocytes were found to be relatively sensitive to HHP; accordingly, a 20-MPa pressure for 60 min proved to be the optimal treatment to increase stress tolerance. The treatment has induced more than tenfold increase in blastocyst rates after vitrification and parthenogenetic activation. In another experiment, pressure-treated oocytes were enucleated and used as recipients for somatic cell nuclear transfer. Both blastocyst rates and the survival of these blastocysts after vitrification have increased significantly. The strongest effect was observed when 1 to 2 h recovery time was applied between the end of the HHP treatment and the initiation of vitrification or enucleation. Transfer of cloned embryos derived from HHP-treated oocytes has resulted in two healthy piglets. Similarly, sublethal HHP stress treatment of immature, GV-stage porcine oocytes resulted in an increased blastocyst rate and higher blastocyst cell numbers following in vitro maturation, parthenogenetic activation, and in vitro culture. In all of these experiments, T2 medium (HEPES-buffered TCM-199 containing 2% cattle serum) was used as holding medium during the HHP treatment of the oocytes.

A recent study has examined the effect of the Cap content of the treatment media used at HHP treatments of porcine oocytes. The efficiency of activation was tested at different pressure levels and media, including T2 and mannitol-PVA fusion medium with (MPVA+Ca2+) or without Ca2+ and Mg2+ (MPVA). The results showed that HHP did not induce parthenogenetic activation in T2 but only in MPVA+Ca2+ with low Ca2+ concentration and MPVA without Ca2+. The highest activation efficiency was achieved with 10 min HHP treatment using 10 or 20 MPa for oocytes in MPVA+Ca2+ or MPVA, respectively. In light of these results, the possible source of Ca2+ during activation was investigated. It was found that even after a total of 30 min wash with TL-HEPES-PVA buffer without Ca2+ before HHP treatment in MPVA, the oocytes could still be activated, indicating the possibility of an intracellular Ca2+ source. It was concluded that parthenogenetic activation could be induced by HHP in certain holding media with low or zero Ca2+ content.

The stress tolerance of mouse oocytes was comparable to that of porcine ones. Treatment of MII phase mouse eggs with 20 MPa pressure for 60 min at 37° C. before vitrification with the Cryotop (Kitazato, Japan) technique has resulted in increased survival after warming and intracytoplasmic sperm injection and increased pregnancy rate and litter size.

First results achieved with HHP treatment and subsequent cryopreservation of mouse embryonic stem cells was also reported. Mouse embryonic stem cells were used to prepare embryoid bodies (EBs). At Day 4 after EB formation, EBs were treated with 60 MPa for 30 min at 24° C. (the same parameters as those used to treat mouse blastocysts) and cryopreserved using the solid surface vitrification technique. After warming, the capability of differentiation into cardiomyocytes was defined by microscopic observation of the beating EBs and cardiomyocyte-specific IHC staining.

Studies showed that the pressure treatment did not affect the survival and the differentiation rate in the nonvitrified groups. However, the applied HHP treatment highly improved the efficiency of in vitro differentiation toward cardiac lineages (74.6% vs. 36.9%, respectively).

DESCRIPTION OF THE FIGURES

FIG. 1 shows the survival rate of embryos at different pressures between 10 MPa and 150 MPa (by 10 MPa) for different times (1 s, 5 min, 15 min and 30 min to 300 min by 30 min intervals), at room temperature. 14-16 embryos were used in each group; each experiment was repeated 3 times. The survival rate of embryos in the fields marked with "a" and "b" is not different from the untreated control ($p<0.05$).

FIG. 2 shows Survival rates of embryos pressurized with 90 MPa for 30, 60, 120 min and decompressed for 30-180 min. (With instant decompression survival at 30, 60 and 120 min was 50%, 0%, 0%, respectively). Survival rates marked on the figure with different superscripts are significantly different from each other ($p<0.05$).

FIG. 3a shows the survival of embryos pressurized with 30, 60 and 90 MPa for 1 sec to 45 min, at room temperature.

FIG. 3b shows the survival of embryos pressurized with 30, 60 and 90 MPa for 1 sec to 45 min, at 0° C. 12-15 embryos were used in each of the groups; each experiment was repeated 3 times. Significant differences are seen between the groups pressurized at room temperature and at 0° C. ($p<0.01$).

FIG. 4 shows the average values of sperm motility (pressurized and control).

FIG. 5 shows the average motility of the sperm of Bull I after pressurization and freezing-thawing.

EXAMPLES

Figure 6:
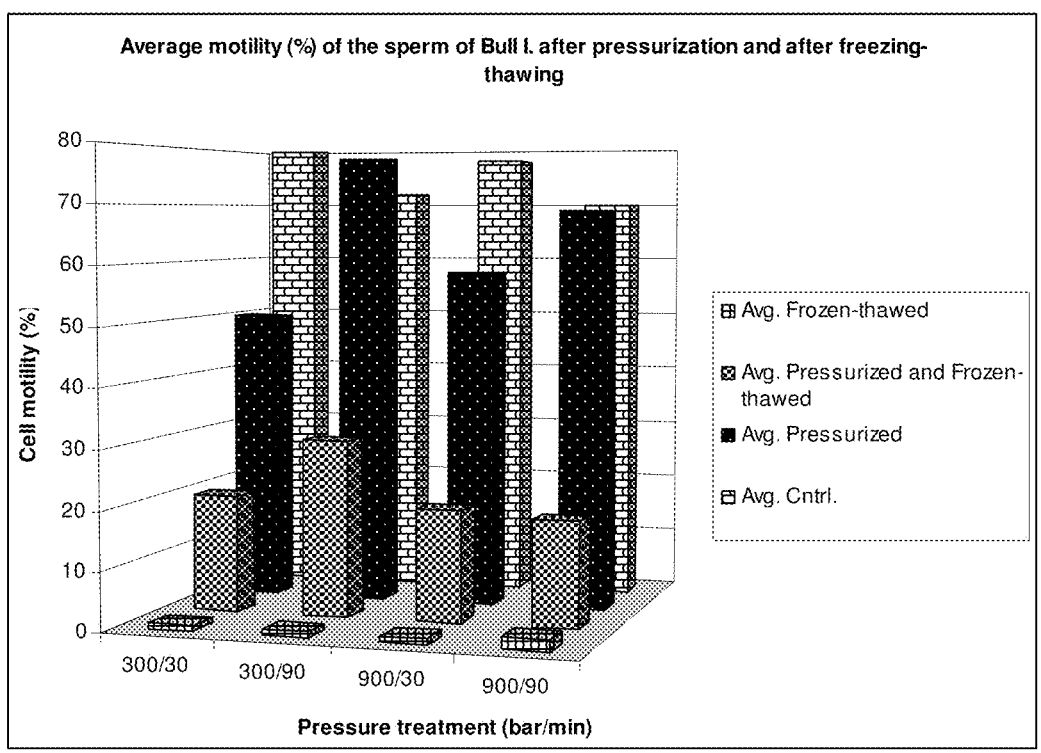
FIG. 6 shows the average motility of the sperm of Bull II after pressurization and freezing-thawing.

Materials and Methods for Examples 1 to 4

Experimental Animals and Embryo Production

CB6F1 (Charles River, Germany) mice were housed under standard conditions (22+/−2° C.; 12 h dark/12 h light; water and food ad libitum).

Females were superovulated by intraperitoneal injection of 10 IU of PMSG (Sigma, USA) followed by 10 IU of hCG (Sigma, USA) 46 h later. After 6 hours of hCG administration, females were mated with fertile males in monogamous pairs. One to two cell stage embryos (Day 0 and Day 1) were harvested by flushing the oviduct with FertiCult Flushing medium (FertiPro N.V., Belgium). Embryos were cultured at 37° C. in thermostat with 5% $CO_2$ and maximal humidity in air. Embryos, between one-cell and compact morula stages, were cultured in G 1.2 medium (Vitrolife, Sweden) under mineral oil, Ovoil (Vitrolife, Sweden). Then, the embryos were transferred and cultured in G 2.2 (Vitrolife, Sweden) under Ovoil until the expanded blastocyst stage. Procedures were approved by the Animal Care and Use Committee of the Faculty.

Pressurization

Blastocysts were loaded into plastic straws without air-bubbles (7-9 embryos/straw), with M2 (Sigma, USA), then straws were heat-sealed. Straws were placed into the pressure-chamber filled with water as pressure medium. The custom-made pressurizing device, which was capable of providing precisely controlled pressure in the range of 1 to 150 MPa was made of stainless steel with the inner diameter of 2 cm, and was connected to a pressure-gauge. Hydrostatic pressure was generated by pushing a piston into the pressure chamber through the manual control of screws. Achieving the desired amount of pressure took from 20 seconds to 5 min (10 MPa to 150 MPa, respectively); the duration of pressure release was 3 seconds. At the experiments where the effects of gradual decompression were investigated, release time was between 30-210 min. At experiments conducted at 0° C., the pressure chamber was simmered in the cooling bath of Bio-cool (FTS-Systems, NY, USA).

Cryopreservation with Previous Pressurization

Embryos were randomly allocated to three groups. Blastocysts of Group I. were cryopreserved as mentioned below, in a vitrification solution containing 7 M Ethylene glycol (EG) according to Nowshari and Brem (1998). Embryos of Group II. were treated with 60 MPa pressure for 30 min, then were frozen in the same way. Group III. served as untreated control. After thawing, embryos were cultured in vitro for 24 hours.

Cryopreservation

Embryos were equilibrated for 5 min in a solution containing 1.5 Methylene glycol (EG) (Sigma, USA) and 0.25 M sucrose in M2 (Sigma, USA), supplemented with 10% Fetal Calf Serum (FCS) (Sigma, USA), then transferred into a vitrification solution (7 M EG, 0.5 M sucrose in M2 with 10% FCS) pre-loaded in a 0.25 ml plastic straw (7-9 embryos/straw). Finally, straws were heat-sealed. After 1 min exposure to the vitrification solution, the straw was slowly immersed in liquid nitrogen. Straws were thawed by transfer into 30° C. water for 30 sec and then the embryos were recovered and placed in rehydration medium (0.5M sucrose in M2 supplemented with 10% FCS) for 5 min. Embryos then were cultured in medium G 2.2 as described above (Nowshari and Brem, 1998).

Embryo Transfer

Embryos were cultured in G 2.2 for 2 hours as above. Then, they were separated in each experimental group as "dead" and "survived" and were transferred separately (7-12 embryos per animal) to Day 3 pseudopregnant recipients. Untreated blastocysts were transferred as controls.

Evaluation and Statistical Analysis

Embryo quality was examined just after releasing the pressure or after thawing and after 2, 3, 4, 6, 12, 20 and 24 hours. The embryo survival was evaluated upon morphological appearance: intactness of the blastomeres re-expansion of the blastocoel, and hatching from the zona pellucida were the signs of survival. Untreated blastocysts were used as controls.

For in vivo evaluation, pressurized embryos were cultured in G 2.2 for 2 hours as above. Then 7-12 embryos per animal were transferred into Day 3 pseudopregnant recipients. Untreated blastocysts were transferred as controls. Birth of healthy pups was proof of in vivo survival of the embryos.

The survival rates were compared to control by chi-square test.

Example 1

Survival of Mouse Embryos at Different Pressures at Room Temperature

In the present experiments embryos were exposed to different hydrostatic pressures from 10 to 150 MPa (by 10 MPa increments) for various times, between 1 sec to 300 min, at room temperature.

The treatment exceeding a certain amount of pressure and time (FIG. 1.) caused reversible morphological changes. The expanded blastocysts compacted inside the zona pellucida: the blastocoel disappeared, the size of the blastomeres reduced but their structural integrity showed no alteration. After 4-5 hours of in vitro culture these blastocysts re-expanded and hatched from the zona pellucida in 24 hours (a). Embryos receiving less impact showed no morphological change and hatched within 24 hours of in vitro culture (b), while embryos challenged with a greater impact did not re-expand from the compacted stage and disintegrated within 2 hours, or were already disintegrated after decompression (c) (FIG. 1).

For in vivo evaluation, challenged embryos were judged "survived" (a&b) and "dead" (c) after 2 hours of in vitro culture after decompression and were transferred into recipients separately. Out of 170 transferred "a" and "b" embryos, 145 healthy pups were born (85%), but 0 were born from 49 "c" embryos (0%).

There were no significant differences between the hatching rate (in vitro) and birth rate (in vivo) of the non pressurized control, the compacted and the non-compacted pressurized "a" and "b" embryos ($p<0.05$).

These results show that embryos can survive a substantial amount of pressure without any change in their survival rate, though the higher the magnitude of the pressure, the less time the embryos survive (FIG. 1.). Embryos that do not disintegrate within 2 hours of in vitro culture have identical in vitro and in vivo survival rates than the untreated controls.

Example 2

Survival of Mouse Embryos after Using Different Decompression Profiles

In the present experiment we investigated whether the survival rate of pressurized embryos could be improved by gradual decompression.

Expanded blastocysts were kept at 90 MPa for 30, 60 and 120 minutes, (where the survival rate at room temperature with instant decompression was 50%, 0% and 0%, respectively) then the pressure was gradually released in 9 steps for 30, 60, 90, 120 and 150 minutes. The results show that survival can be significantly improved by gradual decompression, which has an optimal range depending on the time the embryos spend under pressure. The optimal come-up time rose the longer the time embryos spent under pressure. The maximal survival rate, achievable by decompression, reduced as the time of the pressurization increased. (FIG. 2)

At in vitro evaluation 54 "survived" and 35 "dead" embryos were transferred to 9 recipients. Out of 54 "survived" embryos 47 implanted (87%), but 0 embryos implanted out of the 35 "dead" embryos at the 18 days count. The implantation rate of the "survived" group is not different from that of the controls (p<0.05).

Example 3

Survival of Mouse Embryos at Different Pressures at Low Temperature

In this experiment the role of temperature was investigated on the survival capacity of the pressurized embryos.

30, 60 and 90 MPa pressure was applied to embryos for 1 sec, 5, 10, 15, 30 and 60 min. at low temperature (0° C.). While non-pressurized embryos can live at 0° C. for a substantial amount of time without any significant change in their survival, simultaneous pressure treatment with 30, 60, 90 MPa was lethal for 100% of the embryos after 45, 10, 5 min, respectively. A significantly reduced survival rate was observed with the embryos pressurized at low temperature compared to the groups treated at room temperature (P<0.01%) (FIGS. 3a, 3b).

At in vitro evaluation 40 "survived" and 28 "dead" embryos were transferred to 7 recipients. out of the 40 "survived" embryos 34 implanted (85%), and 0 embryos implanted out of the 28 "dead" embryos at the 18 days count. The implantation rate of the "survived" group is not different from that of the control (p<0.05).

Embryos kept at 0° C. under 90 MPa pressure for 30 minutes were also decompressed gradually. No embryos survived at any of the retrieval times we used (30 60, 90, 120, 150, 180 min). Eight to twelve embryos were used in each group, experiments were repeated for 3 times.

Example 4

Survival of Mouse Embryos after Pressure Treatment, Freezing and Thawing

In the present study we explored whether the survival rate of cryopreserved expanded mouse blastocysts could be improved by pressure treatment before the freezing procedure. Results are presented in Table 1.

TABLE 1

Survival of frozen-thawed embryos cryopreserved with/without previous pressure treatment

| | | Signs of survival after 6 hours | | Signs of survival after 20 hours | | | |
|---|---|---|---|---|---|---|---|
| | n | ½ expanded | Fully expanded | ½ expanded | ⅔ expanded | Fully expanded | Hatched |
| Group I. | 115 | 9% | 0%[b] | 17% | 10% | 19% | 0%[b] |
| Group II. (Pressure treated) | 95 | — | 98%[a] | — | — | 3% | 95%[a] |
| Untreated Control | 107 | — | 99%[a] | — | — | 5% | 94%[a] |

Letters with different superscript are significantly different from each other (p < 0.01)

Significant differences were observed in the survival rate between the pressurized and non pressurized groups (p<0.01). The re-expansion was faster (4-6 hours vs. 20 hours) and the survival rate was higher (98% vs. 46%) in those embryos that received pressure treatment before cryopreservation (Table 1). There was no significant difference between the control and the pressure treated group in the survival and hatching rate.

Example 5

Survival of Bovine Embryos after Pressure Treatment, Freezing and Thawing

Materials and Methods

Oocyte Collection and In vitro Maturation (IVM)

Chemicals were purchased from EMBRAPA (Brasilia, Brazil) unless otherwise indicated. Ovaries were collected from slaughter house and kept in physiological water at 35-37° C. Cumulus-oocyte complexes (COCs) were obtained by aspiration of 2-10 mm follicles using 20 ml syringe with 18 G needle and were collected into 50 ml centrifuge tubes. After 10 minter of sedimentation COCs were aspirated into Petri dishes with TCM-199 Hank's (Gibco) supplemented with fetal calf serum (FCS), penicillin, streptomycin and heparin (Sigma H3149). After the collection COCs were washed three times in the maturation medium (TCM-199 Earl's supplemented with FCS, LH (Sigma), FSH (Sigma), L-Glutamine, penicillin and streptomycin) and were transferred into 2 ml of maturation medium (approximately 100 COCs per Petri dish), covered with mineral oil. Oocites were matured in 38° C. with 5% $CO_2$ and maximal humidity in air for 22 hours.

Sperm Preparation, In Vitro Fertilization (IVF) and In Vitro Culture (IVC)

For IVF, COCs were washed three times in fertilization medium before being transferred in groups of 20-25 into Petri dishes containing four drops of 200 µl of fertilization medium (TALP supplemented with BSA, penicilamin—Sigma P4875, hipotaurin—Sigma H1384, epinefrin—Sigma E4250 and heparin—Sigma H3149) covered with mineral oil. Motile spermatozoa were obtained by centrifugation of frozen-thawed spermatozoa (Gentec, Cuiaba, Brazil) on a Percoll discontinuous density gradient (2 ml of 45% Percoll over 2 ml of 90% Percoll) for 20 min at 700 g at room temperature. Spermatozoa pellet, collected at the bottom of the 90% fraction, were washed in HEPES-buffered Tyrode's and pelleted by centrifugation at 700 g for 5 min. Spermatozoa were counted in a hemocytometer and diluted in the appropriate volume of TALP to give a concentration of $2 \times 10^6$ spermatozoa/ml; a 200 µl aliquot of this suspension was added to each fertilization drop. Plates were incubated for 19 hr in 5% $CO_2$ in humidified air at 39° C. Presumptive zygotes were then cultured in vitro in SOF droplets under mineral oil in a humidified atmosphere of 5% $CO_2$ at 39° C.

Pressurization

Expanded blastocysts were loaded into 0.25 ml plastic straws without air-bubbles (7-9 embryos/straw), with embryo holding medium (Emcare Holding, Emcare, New Zealnd), then straws were sealed with PVC. Straws were placed into the pressure-chamber filled with water as pressure medium. Embryos were exposed to different hydrostatic pressures from 60 to 90 MPa (by 10 MPa increments) for various times (15, 30, 45, 50, 60, 90, 100 minutes), at room temperature, as detailed above.

Cryopreservation with Previous Pressurization

Embryos were randomly allocated to three groups. Blastocysts of Group I were cryopreserved as mentioned below, in a freezing solution containing 1.5 M Ethylene glycol (EG). Embryos of Group II were treated with 80 MPa pressure for 50 min, then were frozen in the same way. The time interval between the beginning of the freezing and the pressure treatment was between 4 to 5 minutes. Group III served as untreated control. After thawing, embryos were cultured in vitro for 24 hours.

Cryopreservation

Blastocysts were equilibrated for 8 minutes in freezing solution consisting of 1.5 Methylene glycol (Emcare, New Zealnd) pre-loaded in a 0.25 ml plastic straw (7-9 embryos/straw). Straws were sealed with PVC. Straws were placed into a programmable freezer (Bio-cool, FTS-Systems, USA, NY) precooled to −5.2° C. After 3 min, seeding was induced.

Following a further 10 min, straws were cooled at −0.5° C./min to −32° C., following which they were plunged into liquid nitrogen. Straws were thawed by 10 sec gentle agitation in air followed by placing the straw into 35° C. water until the ice in the straw melted. Blastocysts were recovered from the straws, washed three times in SOF and were moved to SOF under mineral oil and returned to the incubator for 24 hr.

Evaluation and Statistical Analysis

Embryo quality was examined just after releasing the pressure or after thawing and after 2, 3, 4, 6, 12, and 24 hours. The embryo survival was evaluated upon morphological appearance and continued in vitro development: intactness of the blastocysts, re-expansion of the blastocoel, and hatching from the zona pellucida were the signs of survival. Untreated blastocysts were used as controls.

The survival rates were compared to control by chi-square test. The probability value of $P<0.05$ was taken as statistically significant.

Results

Survival and Continued Development of Embryos after Various Pressure Treatments

In the first set of experiments embryos were exposed to different hydrostatic pressures for various times. Results are summarized in Table 2 below:

TABLE 2

Survival of frozen-thawed bovine embryos cryopreserved with/without previous pressure treatment

| Pressure | Time | n (compacted after decompression/non ~) | continued development 6 h I.-II. | III.-IV. | continued development 24 h (hatched) I.-II. | III.-IV. |
|---|---|---|---|---|---|---|
| 80 MPa | 45 min | 8 (5/3) | 8 | | 8 (4) | |
| 60 MPa | 60 min | 8 (3/5) | 8 | | 8 (5) | |
| 90 MPa | 45 min | 7 (7/0) | 4 | 3 | 4 (1) | 3 |
| 90 MPa | 30 min | 7 (3/4) | 6 | 1 | 6 (6) | 1 |
| control | | 8 | 7 | 1 | 6 (2) | 2 |

I-II: fully or ⅔ re-expanded first of second class embryos
III-IV: third class or dead embryos Continued In Vitro Development of Blastocysts Vitrified with and without Pressure Pre-Treatment In the second study we explored whether the continued in vitro development of cryopreserved expanded in vitro matured/fertilized/cultured bovine blastocysts could be improved by pressure treatment before the freezing procedure. 8-12 embryos were used in each experimental group, experiments were repeated 6 times. Results are presented in Table 3.

Significant differences were observed in the in vitro survival rate between the pressurized and non pressurized groups (p<0.01). The re-expansion was faster (1-2 hours vs. 4-6 hours) and the survival rate was higher (81% vs. 41%) in those embryos that received pressure treatment before cryopreservation (Table 3). There was no significant difference between the control and the pressure treated group in the survival and hatching rate.

TABLE 3

In vitro continued development of IVMFC bovine blastocysts after thawing, frozen with or without pressure pre-treatment

| | | 1 h | | 4 h | | | 12 h | | | 24 h | |
|---|---|---|---|---|---|---|---|---|---|---|---|
| | n | I. + II. | IV. | I. + II. | IV. | Hatched | I. + II. | IV. | Hatched | I. + II. | IV. |
| Frozen with pre-treatment | 59 | 88% | 12% | 81% | 19% | 12% | 81% | 19% | 17% | 81% | 19% |
| Non treated | 61 | 46% | 54% | 41% | 59% | 0% | 41% | 59% | 0% | 41% | 59% |

I-II: fully or ⅔ re-expanded first of second class embryos
IV: dead embryos

Conclusions

Our results showed that the applied pressure treatment prior to freezing could improve the in vitro developmental speed, survival and hatching rates of the IVMFC (in vitro maturation of the oocytes, in vitro fertilization, in vitro culture of embryos) bovine embryos. This study provides further evidence that a pressure impulse can greatly add to the success of cryopreservation. It is appreciated that the methods presented in the above experiments are easily adaptable to a whole range of biological material, in particular embryos of different origin, for example equine, caprine, swine or primate, including human embryos.

Example 6

Survival of Sperm after Pressure Treatment, Freezing and Thawing

In the first part of the present study we intended to describe how HHP affects the ratio of the motile cells of the fresh bull semen. In the second part of the experiment we have chosen 4 parameter-pairs from the pressure-time-sperm motility chart drawn up, and compared the post-thaw motility of the frozen bull-semen pre-treated with the chosen pressure-time parameters with the ones that were frozen without pre-treatment.

Samples of semen were obtained at the Artificial Insemination Centre of Klessheim, Austria. Sample was diluted to a sperm concentration of $8 \times 10^7$/ml with AndroMed extender (MiniTub, Germany) as described in the prescription. The diluted sperm was loaded into 0.25 ml straws and kept at room temperature. Before the pressure treatment the straw with the semen sample was cut into two parts. One half was heat sealed and then pressurized with a specific pressure/time parameter, the other half was used to compare the post-pressure motility. Experiments at each pressure/time parameters were repeated for seven times, progressive motility was assessed individually by light microscopic investigation by two separate assistants. The treatment groups were challenged with the following parameters: 10 MPa for 30, 60, 90 and 120 min; 30 MPa for 30, 60, 90, 120 and 510 min; 50 MPa for 30, 60 and 90 min; 70 MPa for 30, 60 and 90 min; 90 MPa for 30, 60, 90, 120 and 510 min. The pressurizing device was custom made of stainless steel, comprising a pressure chamber with water as a pressure medium, and an authority-approved pressure gauge. The time of reaching the desired amount of pressure was between one to five minutes, depressurization took between two to three seconds.

The average motility of the control samples ranged between 75 to 90 percent, while the average motility of the pressurized samples ranged between 55 (90 MPa/120 min) to 84 (10 MPa/30 min) percent. The groups of 30 MPa/510 min and 90 MPa/510 min had significantly reduced motility compared to the other pressurized groups (27% and 33%, respectively; p<0.05). See FIG. 4.

In the second part of the trial samples of semen were obtained from two bulls (one with a history of very poor freezability). Samples were diluted as above, than were divided into four treatment groups. The treatment groups were split: one half was heat sealed and pressurized with I: 90 MPa/30 min; II: 90 MPa/90 min; III: 30 MPa/30 min; IV: 30 MPa/90 min prior to freezing, the other half was frozen without pre-treatment with the same freezing protocol (60 min equilibration at 5° C., then 10 minutes at −110° C. before plunging into liquid nitrogen). Thawing was performed in 35° C. water-bath for 30 seconds. Each group was also tested for initial motility with and without pressurization. Each trial was repeated for eight times.

The average initial motility of both of the bulls was between 65 and 80 percent, while after pressurization it has reduced to between 45 to 75 percent. The average post thaw motility of both of the bulls was significantly superior with pressure pre-treatment compared to the samples frozen without previous pressurization (p<0.001) (Bull I: 2-3% without pressurization vs. 17-33% with pressurization; Bull II: 0% without pressurization vs. 21-35% with pressure pre-treatment). Amongst the parameters used, 30 MPa/90 min proved significantly superior (33 and 35%; p<0.05).

The present study clearly describes the beneficial effect of a previous pressure treatment to the post thaw motility of bull semen cryopreserved in our experiment. This study provides further evidence that a pressure impulse can greatly add to the success of cryopreservation. It is appreciated that the methods presented in the above experiments are easily adaptable to a whole range of biological material, in particular sperms of different origin, for example equine, caprine, swine or primate, including human origin.

Example 7

HHP Stress Tolerance of Porcine Oocytes and HHP Stress-Treatment Increase in their Cryosurvival 1. Materials and Methods All chemicals except where otherwise indicated were obtained from Sigma Chemical Co. (St. Louis, Mo., USA).

1.1. Oocyte Collection and In Vitro Maturation (IVM)

Cumulus—oocyte complexes (COCs) were aspirated from 2 mm to 6 mm follicles from slaughterhouse-derived sow ovaries. COCs were matured in groups of 50 in 400 ml bicarbonate buffered TCM-199 (GIBCO BRL) supplemented with 10% (v/v) cattle serum (CS), 10% (v/v) pig follicular fluid, 10 IU/ml eCG, 5 IU/ml hCG (Suigonan Intervet; Skovlunde, Denmark) at 38.5° C. in the "Submarine Incubation System" (SIS; Vajta et al., 1997) in 5% CO2 in humidified air for 41-44 h.

1.2. Oocyte Treatment with Hydrostatic Pressure Pulse

Oocytes in Hepes buffered TCM199 (TCMH) medium were aspirated with a 2 ml syringe into 0.5 ml straws. Straws were then placed into the pressure chamber of one of the pressurizing devices (Cryo-Innovation Inc. Budapest, Hungary), containing water as pressure medium. Hydrostatic pressure was applied at the rate of 10 MPa/min, followed by constant holding of the pressure for various times between 30 min and 120 min (Tables 4 and 6), then decompression to atmospheric pressure at 10 MPa/min.

TABLE 4

Effect of different hydrostatic pressure-time treatment-combinations on the cleavage rates of activated porcine oocytes (Experiment I)

| P/t at 24° C. | 30 min | 60 min | 120 min |
| --- | --- | --- | --- |
| 20 MPa | 18/43 (42%)** | 27/50 (54%)*** | 16/61 (26%)* |
| 40 MPa | 17/49 (35%)** | 22/62 (36%)** | 14/48 (29%)* |
| 60 MPa | 0/37 (0%) | 0/39 (0%) | 0/43 (0%) |
| 80 MPa | 0/44 (0%) | 0/47 (0%) | |
| Control at 24° C. in straw | 11/59 (19%) | | |
| Control in thermostat | 4/41 (10%) | | |

Groups marked with "*" differ significantly from the thermostat control (*P < 0.05; P < 0.01; *P < 0.001).

1.3. Oocyte Activation

Forty-one hours after the start of IVM, cumulus investments of the COCs were removed by repeated pipetting in 1 mg/ml hyaluronidase in TCMH. From this point (except where otherwise indicated) all manipulations were performed on a heated stage adjusted to 39° C. Oocytes were equilibrated for 10 s in activation medium (0.3 M mannitol, 0.1 mM MgSO4, 0.1 mM CaCl2 and 0.01% PVA) and transferred to a fusion chamber (BTX microslide 0.5 mm fusion chamber, model 450; BTX, San Diego, Calif., USA). A single direct current (dc) pulse was generated with a BLS CF-150/B cell fusion machine (BLS, Budapest, Hungary). Activated embryos were transferred into PZM-3 medium (Yoshioka et al., 2002) supplemented with 5 mg/ml cytochalasin B and 10 mg/ml cycloheximide. After a 4 h incubation at 38.5° C. in 5% CO2, 5% O2 and 90% N2 with maximum humidity, embryos were washed 3 times and cultured in 400 ml PZM-3 medium covered with mineral oil, at 38.5° C. in 5% CO2, 5% O2 and 90% N2 with maximum humidity.

1.4. Oocyte Vitrification

Cryopreservation was carried out by vitrification with a Cryotop device and factory-prepared vitrification and warming solutions (Kitazato Supply Co., Fujinomiya, Japan) as described previously (Kuwayama et al., 2005a,b). Oocytes were transferred into equilibration solution (ES) consisting of 7.5% ethylene glycol (EG) and 7.5% dimethylsulfoxide (DMSO) in TCMH medium supplemented with 20% synthetic serum substitute (SSS; Cat. No. 99193, Irvine Scientific, Santa Ana, Calif.) at 39° C. for 5-15 min. Ten to twenty oocytes were then transferred into 20 µl drop of vitrification solution (VS) consisting of 15% EG, 15% DMSO and 0.5 M sucrose dissolved in TCMH medium and 20% SSS. After incubation for 20-30 s, oocytes were loaded on Cryotop and plunged into liquid nitrogen. The process from exposure in VS to plunging was completed within 1 min.

Vitrified oocytes were warmed by immersing Cryotop directly into 39° C. thawing solution (1.0 M sucrose dissolved in TCMH medium and 20% SSS) for 1 min, then transferred to dilution solution (0.5 M sucrose dissolved in TCMH and 20% SSS) for 3 min. Subsequently, oocytes were incubated twice for 5 min in the washing solutions (TCMH and 20% SSS).

1.5. Experiment I

Experiment I was conducted to see if pressure treatment can improve the developmental competence of oocytes if sub-optimal parthenogenetic activation is used. COCs were randomly distributed between 11 treatment groups and 2 control groups. Those in treatment groups were loaded into straws as described above, cooled to 24° C. in 15 min and put into one of the 11 pressurizing machines. Treatments were done simultaneously according to Table 4. COCs of one of the control groups were loaded into straw and kept for 120 min at 24° C. as described above. For the other control group, oocytes were incubated at 38.5° C. under conditions as described earlier. After these treatments cumulus cells were removed and oocytes were activated with an electric pulse that is 10 times of what is routinely used for pig oocyte activation. The parthenogenetic activation and embryo culture system used in our laboratory is capable to produce 80% blastocyst rates under normal condition. Any improvement is difficult to detect if the basic system is working with such a high efficiency. Accordingly, we changed our activation parameters by increasing the dc impulse tenfold, from the standard 1.25 kV/cm to 12.5 kV/cm. By using this drastic impact we could test shock tolerance of the treated vs. control oocytes and also compare their developmental competence in vitro. After activation, presumptive zygotes were cultured in vitro until day 7. Three identical replicates were performed by using a total of 620 oocytes. The number of oocytes per group was between 13 and 21.

1.6. Experiment II

Experiment II was conducted to see how different pressure treatments at 24° C. or 38° C. effect oocyte survival after vitrification/warming. Denuded oocytes were randomly distributed between 12 treatment groups and 3 control groups. Those of the 12 treatment groups were loaded into straws as described above, and put into one of the 12 pressurizing machines. The temperatures of 6 machines were set to 24° C.; other 6 machines were set to 38° C. Treatments were done simultaneously according to Table 6. Two of the control groups were kept for 120 min at 24° C. or 38° C., respectively, loaded into straws as described above. The third control group was left in the thermostat unaffected. After the treatment oocytes were vitrified, warmed and activated with a single dc of 1.25 kV/cm for 80 ms. Then, presumptive zygotes were treated with cytochalasin B and cycloheximide as described above and cultured in vitro until day 7. Five identical replicates were performed by using a total of 1360 oocytes. The number of oocytes per group was between 15 and 20.

1.7. Evaluation and Statistics

Data were analyzed by a generalized linear model (logistic regression) (Venables and Ripley, 2002).

The only independent factor was the time-pressure interaction (the treatments separately) that was tested by a likelihood ratio test in each experiment. All statistical calculations were done in R 2.4.1. (R Development Core Team, 2006). P levels lower than 0.05 were regarded as significant.

2. Results

2.1. Experiment I

Effects of treatments are presented in Tables 4 and 5. The effect of the time-pressure treatment combinations was significant both on cleavage and blastocyst rates of the oocytes (P<0.001). The largest cleavage and blastocyst rates were obtained in the 30 min/20 MPa and 60 min/20 MPa treated groups. Following the 60 MPa and 80 MPa treatments no oocytes survived. No statistical significance was observed between the two control groups (P=0.22).

TABLE 5

Blastocyst formation rates of treatment groups treated with different hydrostatic pressure-time parameters, followed by parthenogenetic activation of porcine oocytes (Experiment I)

| P/t at 24° C. | 30 min | 60 min | 120 min |
|---|---|---|---|
| 20 MPa | 20/43 (47%) * | 23/50 (46%) * | 18/60 (30%) |
| 40 MPa | 13/49 (27%) | 22/62 (36%) | 13/46 (28%) |
| 60 MPa | 0/37 (0%) | 0/39 (0%) | 0/41 (0%) |
| 80 MPa | 0/44 (0%) | 0/47 (0%) | |
| Control at 24° C. in straw | 16/57 (28%) | | |
| Control in thermostat | 9/41 (22%) | | |

Groups marked with "*" differ significantly from the thermostat control (P < 0.05).

2.2. Experiment II

Cleavage rates of the different treatment combinations followed by vitrification and parthenogenetic activation of oocytes are presented in Table 6. The effect of the time-pressure treatment combinations was significant on the cleavage rate of the oocytes treated either at 24° C. or at 38° C. The highest cleavage rate was observed after 60 min/40 MPa treatment at 24° C. The effect of pressure treatment on blastocyst rates was not significant neither at 24° C., nor at 38° C. treatments (P=0.62 and 0.14, respectively) (Table 7).

TABLE 6

Effect of different hydrostatic pressure-time treatment-combinations on the cleavage rates of vitrified-warmed-activated porcine oocytes (Experiment II)

| P/t at 24° C. | 30 min | 60 min | 90 min | P/t at 38.5° C. | 30 min | 60 min | 90 min |
|---|---|---|---|---|---|---|---|
| 20 MPa | 12/87 (14%) | 15/81 (19%)* | 9/83 (11%) | 20 MPa | 14/86 (16%) | 18/85 (21%)* | 18/86 (21%)* |
| 40 MPa | 14/86 (16%) | 25/91 (27%)** | 16/87 (18%)* | 40 MPa | 12/88 (14%) | 7/86 (8%) | 17/83 (20%)* |
| Control at 24° C. in straw | 8/81 (10%) | | | Control at 38.5° C. in straw | 4/81 (5%) | | |
| Control in thermostat | 7/87 (8%) | | | | | | |

Groups marked with "*" differ significantly from the thermostat control (*P < 0.05; **P < 0.01).

TABLE 7

Blastocyst formation rates of treatment groups treated with different hydrostatic pressure-time parameters, followed by vitrification-warming and parthenogenetic activation (Experiment II)

| P/t at 24° C. | 30 min | 60 min | 90 min | P/t at 38.5° C. | 30 min | 60 min | 90 min |
|---|---|---|---|---|---|---|---|
| 20 MPa | 1/87 (1%) | 0/81 (0%) | 0/83 (0%) | 20 MPa | 0/86 (0%) | 2/85 (2%) | 1/86 (1%) |
| 40 MPa | 1/86 (1%) | 1/91 (1%) | 1/83 (1%) | 40 MPa | 0/88 (0%) | 0/86 (0%) | 3/83 (4%) |
| Control at 24° C. in straw | 0/81 (0%) | | | Control at 38.5° C. in straw | 1/81 (1%) | | |
| Control in thermostat | 0/87 (0%) | | | | | | |

Example 8

HHP Treatment Improves Considerably the Cryosurvival of Porcine Oocytes

1. Materials and Methods

Unless otherwise indicated, all chemicals were purchased from Sigma Chemical Co.

1.1. Oocyte Collection and IVM

Cumulus—oocyte complexes (COCs) aspirated from 2 to 6 mm follicles from slaughterhouse-derived sow ovaries were matured in groups of 50 in 400 ml bicarbonate-buffered TCM-199 supplemented with 10% (v/v) cattle serum, 10% (v/v) pig follicular fluid, 200 mM glutamine, 10 IU/ml eCG and 5 IU/ml hCG (Suigonan Intervet; Skovlunde, Denmark) at 38.5 8 C in the Submarine Incubation System (SIS; Vajta et al. 1997) in 5% CO2 in humidified air for 41-44 h.

1.2. COC Treatment with HHP

Expanded COCs in HEPES-buffered TCM-199 (TCMH) were loaded into 0.5 ml plastic straws with a 2 ml syringe. Straws were then placed into the pressure chamber of the pressurizing device (Cryo-Innovation Inc., Budapest, Hungary), containing water as pressure medium. The chamber was made of stainless steel with an inner diameter of 2 cm and was connected to a pressure gauge. Pressure was generated by a moving piston inside the pressure chamber at the speed of 1 min/10 MPa. When the required pressure was reached it was maintained continuously for the specified period. The rate of decompression to atmospheric pressure was 1 min/10 MPa. After HHP treatments, COCs were released from straws and incubated in the original IVM medium until the start of the next procedure.

1.3. Oocyte Denudation and Vitrification

The cumulus investment of the COCs was removed by repeated pipetting in 1 mg/ml hyaluronidase in TCMH. From this point (except where otherwise indicated), all manipulations were performed on a heated stage adjusted to 39° C. Cryopreservation was carried out by vitrification with a Cryotop device and factory-prepared vitrification and warming solutions (Kitazato Supply Co., Fujinomiya, Japan) as described previously (Kuwayama et al. 2005). Oocytes were transferred into equilibration solution (ES) consisting of 7.5% ethylene glycol (EG) and 7.5% dimethylsulfoxide (DMSO) in TCMH and 20% synthetic serum substitute (SSS; Cat. No. 99193, Irvine Scientific, Santa Ana, Calif., USA) at 39° C. for 5-15 min. After an initial shrinkage, oocytes regained their original volume. Ten to twenty oocytes were transferred into a 20 ml drop of vitrification solution (VS) consisting of 15% EG, 15% DMSO, and 0.5 M sucrose dissolved in TCMH and 20% SSS. After incubation for 20-30 s, oocytes were loaded on Cryotop and plunged into liquid nitrogen. The process from VS exposure to plunging was completed within 1 min.

Vitrified oocytes were warmed by immersing Cryotop directly into 39° C. thawing solution (1.0 M sucrose dissolved in TCMH and 20% SSS) for 1 min and then transferred to dilution solution (0.5 M sucrose in TCMH and 20% SSS) for 3 min. Subsequently, oocytes were incubated twice for 5 min in the washing solutions (TCMH and 20% SSS).

1.4. PA and Embryo Culture

After warming, oocytes were equilibrated shortly in activation medium drops (0.3M mannitol, 0.1 mM MgSO4, 0.1 mM CaCl2, and 0.01% polyvinyl alcohol) for 5 s. Under a 1.25 kV/cm alternative current, oocytes were aligned to the wire of a fusion chamber (Microslide 0.5 mm fusion chamber, model 450; BTX, SanDiego, Calif., USA). Then a single direct current pulse was applied to the oocytes for electrical activation. After washing thrice in drops of TCMH supplemented with 10% calf serum, activated oocytes were incubated in culture medium (PZM-3 medium supplemented with 4 mg/ml BSA), 5 mg/ml cytochalasin B, and 10 mg/ml cycloheximide at 38.5° C. in 5% $CO_2$, 5% $O_2$, and 90% $N_2$ with maximum humidity. After 4 h treatment, embryos were washed and then cultured in culture medium.

1.5. Embryo Evaluation

Cleavage rates were evaluated on day 2. Blastocyst rates were recorded after 8 days of culture. To determine total cell numbers, day 8 blastocysts were fixed and mounted on a glass microscopic slide in glycerol containing 20 mg/ml Hoechst 33342 fluorochrome. After staining for 24 h, embryos were observed under a Diaphot 200 inverted microscope with epifluorescence attachment and UV-2A filter (Nikon, Tokyo, Japan).

1.6. Experimental Design

Experiment 1

Based on our previous experience in HHP tolerance of porcine IVM oocytes, 20 and 40 MPa pressure lasting for 60 min were applied in the first experiment, with recovery times of 10, 70, and 130 min between pressurization and vitrification. Two control groups were used, one untreated vitrification control and one direct activation control. At least three repeat experiments were performed for each group.

Experiment 2

Parameters resulting in the highest cleavage and blastocyst rate in experiment 1 were applied in experiment 2. HHP was performed at either 37 or 25° C. to investigate possible influence of treatment temperature. Three control groups were set up. Oocytes loaded in straws without HHP treatment were kept either at 37 or 25° C. and used as vitrification control (37° C. vitrification group, 25° C. vitrification group). Oocytes with neither HHP nor vitrification were parthenogenetically activated directly as activation controls. The experiments were performed with three replicates.

1.7. Statistical Analysis

Data were analyzed by a generalized linear model of SAS 9.1 (SAS Institute Inc., Cary, N.C., USA). A probability of P<0.05 was considered to be statistically significant.

2. Results

The optimal parameters of HHP for improved survival and development of vitrified porcine IVM oocytes were investigated in the first experiment. As shown in Table 8, vitrified oocytes had severely reduced developmental competence when compared with fresh oocytes, regardless of HHP treatment. However, those oocytes that were pretreated with HHP (20 MPa, 60 min) and recovered for 70 or 130 min had a significantly improved in vitro development (P<0.01) when compared with the vitrification control group as evaluated by cleavage rates (38.4+/−6.8% for 70 min group, 41.7+/−6.5% for 130 min group versus 14.5+/−5.2% for vitrification control) and blastocyst rates (11.4+/−2.4% for 70 min group, 13.1+/−3.2% for 130 min group versus 0.0+/−0.0% for vitrification control). Comparable cell numbers were obtained in blastocysts produced from these two groups (37.5+/−3.4 for 70 min group, 36.6+/−3.7 for 130 min group), which were significantly less than observed in the activation control group (55.7+/−4.0) where fresh oocytes were activated.

TABLE 8

In vitro development of vitrified-warmed porcine in vitro matured oocytes after being pretreated with high hydrostatic pressure under various parameters.

| Pressure magnitude (MPa) | Recovery duration (min) | No. of treated oocytes | Cleavage rate (%, mean ± S.E.M.) | Blastocyst rate (%, mean ± S.E.M.) | Cell no. |
| --- | --- | --- | --- | --- | --- |
| 20 | 10 | 166 | 11.2 ± 3.5$^b$ | 1.9 ± 0.8 | — |
|  | 70 | 190 | 38.4 ± 6.8$^c$ | 11.4 ± 2.4 | 37.5 ± 3.4$^b$ |
|  | 130 | 201 | 41.7 ± 6.5$^c$ | 13.1 ± 3.2 | 36.6 ± 3.7$^b$ |
| 40 | 10 | 77 | 16.2 ± 3.2$^b$ | 5.9 ± 3.1 | — |
|  | 70 | 78 | 26.3 ± 4.5$^b$ | 5.2 ± 3.1 | — |
|  | 130 | 93 | 25.1 ± 4.1$^b$ | 5.3 ± 0.9 | — |
| Vitrification control | — | 142 | 14.5 ± 5.2$^b$ | 0.0 ± 0.0 | — |
| Activation control | — | 161 | 86.9 ± 2.9$^a$ | 81.5 ± 9.1 | 55.7 ± 4.0$^a$ |

Different superscripts within the same column denote significant difference (P < 0.05).

In the second experiment, a possible temperature effect on HHP treatment was investigated. HHP parameters resulting in the best results in the first experiment (20 MPa 60 min, with 70 min recovery before vitrification) were applied. When HHP treatment was performed at 37° C., a significantly higher blastocyst rate (14.1+/−1.4%) was obtained than that observed with HHP treatment at 25° C. (5.3+/−1.1%) and in the vitrification groups (Table 9).

TABLE 9

In vitro development of vitrified-warmed porcine in vitro matured oocytes after being pretreated with high hydrostatic pressure (HHP, 20 MPa for 60 min, recovered for 70 min) under different temperatures.

| Group | No. of treated oocytes | Cleavage rate (%, mean ± S.E.M.) | Blastocyst rate (%, mean ± S.E.M.) |
| --- | --- | --- | --- |
| 37° C. HHP | 127 | 45.1 ± 8.4$^a$ | 14.1 ± 1.4$^a$ |
| 25° C. HHP | 126 | 33.5 ± 10.8$^a$ | 5.3 ± 1.1$^b$ |
| Vitrification control | 100 | 21.8 ± 15.6$^b$ | 1.3 ± 1.3$^b$ |
| 25° C. | 98 | 4.4 ± 2.9$^c$ | 0.8 ± 0.8$^b$ |

TABLE 9-continued

In vitro development of vitrified-warmed porcine in vitro matured oocytes after being pretreated with high hydrostatic pressure (HHP, 20 MPa for 60 min, recovered for 70 min) under different temperatures.

| Group | No. of treated oocytes | Cleavage rate (%, mean ± S.E.M.) | Blastocyst rate (%, mean ± S.E.M.) |
|---|---|---|---|
| vitrification control | | | |
| PA CK | 109 | $89.3 \pm 5.2^d$ | $80.0 \pm 2.1^c$ |

Different superscripts within the same column denote significant difference (P < 0.05). PA CK, activation control.

Example 9

HHP Treatment Improves Considerably the Cryosurvival of Mouse and Human Oocytes Objective—Sublethal environmental stress induces general adaptation of cells and makes them more resistant during subsequent interventions such as cryopreservation.

In the present study controlled, sublethal hydrostatic pressure (HP) stress was used to treat mouse and human oocytes before vitrification in order to increase post-warming survival and developmental competence.

Design—Eggs were HP treated, then vitrified using the Cryotop technique (mouse) or cryopreserved (MediCult's Oocyte Freezing kit) (human). After warming eggs were fertilized by ICSI, cultured till the blastocyst stage or transferred to surrogate mothers (mouse); or parthenogenetically activated (PA) (human) Gene expression changes in the treated mouse were studied with microarray. Untreated eggs served as controls.

Material & methods—Stress treatments were performed in a programmable HP machine (Cryo-Innovation Inc., Budapest, Hungary) with 20 MPa for 60 minutes at 37° C.

PA: 10 µM Calcimicin treatment for 5 min, followed by 5 mM DMAP for 3 hours.

ICSI was performed by using a Piezo-driven system (Kuretake et al., 1996).

Microarray: 4×44k whole mouse genome chip was used (Agilent Technologies, Palo Alto, USA) for RNA hybridization, validated by RT-qPCR. 50 eggs were used in 4 replicates.

Procedures were approved by the Animal Care and Use Authority and the Ethical Committee of the supervising Medical University, respectively. T test was used for statistical analysis, results were significant if p<0.05.

Results—HP treatment has improved cleavage rates both in mouse and human, and birth rates in the mouse.

| | n | survived | cleaved | Born |
|---|---|---|---|---|
| Mouse Control | 174 | 71% | 42% | 12% |
| Mouse HP | 184 | 73% | 51% | 27% |
| Human Control | 34 | 73.50% | 32% | — |
| Human HP | 16 | 87.50% | 50% | — |

There was no change in the gene-expression profile of the HP-treated oocytes compared to untreated controls.

Conclusions—Sublethal HP stress treatment enhances the developmental competence of mouse and human oocytes after vitrification/warming. HP-treatment related alterations were not detected in the gene-expression of the oocytes.

Sublethal HHP stress treatment of human eggs (and other reproductive cells) can be a useful and safe tool to enhance the efficacy of cryopreservation.

Example 10

High Hydrostatic Pressure Treatment of Porcine Oocytes before Cloning Improves Developmental Competence and Cryosurvival 1. Materials and Methods Except where otherwise indicated, all chemicals were obtained from Sigma Chemical Co. (St. Louis, Mo.); all manipulations were performed on a heated stage adjusted to 39° C.; and all drops used for handling oocytes were 20 µL covered with mineral oil.

1.1 Oocyte Collection and In Vitro Maturation (IVM)

Cumulus-oocyte complexes (COCs) were aspirated from 2- to 6-mm follicles from slaughterhouse-derived sow ovaries and matured in groups of 50 in 400 µL in vitro maturation (IVM) medium consisting of bicarbonate-buffered TCM-199 (Gibco BRL, Gaithersburg, Md.) supplemented with 10% (v/v) cattle serum (CS), 10% (v/v) pig follicular fluid, 10 IU/mL eCG, 5 IU/mL hCG (Suigonan Vet; Skovlunde, Denmark) at 38.5° C. in 5% CO2 in humidified air in the Submarine Incubation System (SIS; Vajta et al., 2004) for 41-44 h.

1.2. High Hydrostatic Pressure Treatment

Matured oocytes were randomly distributed into two groups. Half of them were loaded into a 0.5-mL plastic straw without air bubbles (100-110 COCs/straw), with T2 (T for HEPES-buffered TCM-199; the number means percentage (v/v) of cattle serum supplementation, here 2%). Then the straw was sealed with stainless steel globes. The straw was placed into a preheated stainless steel pressure chamber filled with water as pressure medium. COCs were exposed to 20 MPa for 1 h at 37° C. Subsequently HHP-treated COCs were recovered in IVM medium for 1 or 2 h (HHP1 and HHP2 group) before the next manipulation. Control oocytes were continuously incubated in maturation medium as described above.

1.3 Oriented Handmade Enucleation

Both control and HHP treated COCs were shortly treated with 1 mg/mL hyaluronidase and pipetted vigorously to remove the cumulus cell attached to the zona pellucida. Zonae pellucidae of both groups of oocytes were partially digested with 3.3 mg/mL pronase solution dissolved in T33 for 20 s, then washed quickly in T2 and T20 drops. Oocytes with distended and softened zonae pellucidae were lined up in T2 drops supplemented with cytochalasin B. With a finely drawn and fire-polished glass pipette, oocytes were rotated to locate the polar body on the surface. Oriented bisection was performed manually with Ultra Sharp Splitting Blades (AB Technology, Pullman, Wash.) under a stereomicroscope. Less than half of the cytoplasm close to the polar body was removed from the remaining putative cytoplast.

1.4. Fusion and Initiation of Activation

Suspension of porcine fetal fibroblast cells were obtained by trypsin digestion of monolayers as described previously (Kragh et al., 2005). The cells were allowed to settle in 20 µL drop of T2. Fusion was performed in two steps, where the second one included the initiation of activation, as well. For the first step, 50% of the available cytoplasts were transferred into 1 mg/mL of phytohemagglutinin (PHA; ICN Pharmaceuticals, Girraween, Australia) dissolved in TO for 3 sec, and then each one was quickly dropped over a single fibroblast cell. After attachment, cytoplast-fibroblast pairs were equilibrated in fusion medium (0.3 M mannitol and 0.01% PVA) for 10 sec and transferred to a fusion chamber (BTX microslide 0.5 mm fusion chamber, model 450; BTX, SanDiego, Calif.). Using an alternating current (AC) of 0.6 kV/cm and 700 kHz, pairs were aligned to the wire of the fusion chamber with the somatic cells farthest from the wire, then fused with a direct current of 2.0 kV/cm for 9 msec. After the electrical pulse, pairs were removed carefully from the wire, transferred to T10 drops, and incubated further to observe whether fusion had occurred.

Approximately 1 h after the first fusion, each pair was fused with another cytoplast in activation medium (0.3 M mannitol, 0.1 mM MgSO4, 0.1 mM CaCl2, and 0.01% PVA). By using an AC of 0.6 kV/cm and 700 kHz, one fused pair and one cytoplast was aligned to one wire of the fusion chamber, with fused pairs contacting the wire. A single DC pulse of 0.85 kV/cm was applied for 80 msec. When fusion had been observed in T10 drops, reconstructed embryos were transferred into porcine zygote medium 3 (PZM-3; Yoshioka et al., 2002) supplemented with 5 mg/mL cytochalasin B and 10 mg/mL cycloheximide. After a 4-h incubation at 38.5° C. in 5% CO2, 5% O2, and 90% N2 with maximum humidity, embryos were washed three times in PZM-3 medium before culture.

1.5. Embryo Culture and Evaluation

Embryos were cultured at 38.5° C. in 5% O2, 5% CO2, and 90% N2 with maximum humidity in PZM-3 medium in well of well system (WOWS; Vajta et al., 2000). Blastocyst rates were examined under a stereomicroscope on Day 6 (D6 blastocysts). To determine total cell numbers, blastocysts were fixed and mounted on a glass microscopic slide in glycerol supplemented with Hoechst 33342 fluorochrome. After staining for 24 h, embryos were observed under a Diaphot 200 inverted microscope with epifluorescent attachment and UV-2A filter (Nikon, Tokyo, Japan).

1.6. Vitrification of Embryos

Cryopreservation was carried out by vitrification with a Cryotop device and factory-prepared vitrification and warming solutions (Kitazato Supply Co., Fujinomiya, Japan) as described previously (Kuwayama et al., 2005a, 2005b). Blastocysts were transferred into equilibration solution (ES) consisting of 7.5% ethylene glycol (EG) and 7.5% dimethylsulfoxide (Me2SO) in T0 and 20% synthetic serum substitute (SSS; Cat. No. 99193, Irvine Scientific, Santa Ana, Calif.) at 39° C. for 5 to 15 min. After an initial shrinkage, blastocysts regained their original volume. Four to six blastocysts were then transferred into 20 µL drop of vitrification solution (VS) consisting of 15% EG, 15% Me2SO, and 0.5 M sucrose dissolved in T0 and 20% SSS. After incubation for 20-30 sec, blastocysts were loaded on Cryotop and plunged into liquid nitrogen. The process from exposure in VS to plunging was completed within 1 min.

Vitrified blastocysts were warmed by immersing Cryotop directly into 39° C. thawing solution (1.0 M sucrose dissolved in T0 and 20% SSS) for 1 min, then transferred to dilution solution (0.5 M sucrose dissolved in T0 and 20% SSS) for 3 min. Subsequently, blastocysts were incubated twice for 5 min in the washing solutions (T0 and 20% SSS). Survival of vitrified blastocysts was determined according to their reexpansion rates after 18-24 h recovery in PZM-3 medium supplemented with 10% CS.

1.7. Embryo Transfer

D5, D6, and D7 fresh blastocysts produced from the HHP2 group were surgically transferred into one uterine horn of Danish landrace sows on day 4 after weaning. Pregnancy was diagnosed by ultrasonography on day 21 and confirmed every second week. The farrowing was induced with an injection of prostaglandin if the sow did not show labor as late as day 121.

All animals were housed and cared for in strict accordance to the proposals for animal research reviewed by Danish Institute of Agricultural Sciences and the Danish Centre for Bioethics and Risk Assessment. Experimental permission was given by the Danish Animal Ethics Committee.

1.8. Statistical Analysis

Statistical analysis was performed using SPSS 13.0 (SPSS, Chicago, Ill.). A t-test was performed to analyze difference in blastocyst rate, cryosurvival rate, and cell number. A probability of $p<0.05$ was considered to be statistically significant.

1.9. Experimental Design

In Experiment 1, HHP treated versus control oocytes were used for HMC in three replicates in HHP1 and five replicates in HHP2 groups (1 and 2 h recovery, respectively). Six days after reconstruction, blastocyst rate were recorded. Fresh blastocysts derived from HHP-treated oocytes (HHP1 group) were transferred into two recipient sows (56 for one sow and 57 for another).

In Experiment 2, randomly selected D6 blastocysts in HHP2 group and control group were fixed and cell numbers were counted under a stereomicroscope after Hoechst staining. Remaining blastocysts in both HHP2 and control group were vitrified with the Cryotop method. Survival rates of reexpanded blastocysts were determined 18-24 h after warming and in vitro culture.

2. Results

In Experiment 1, 90, 144, and 204 reconstructed embryos were produced from the HHP1, HHP2 and control oocytes, respectively (Table 10). Developmental rate to blastocysts was higher in HHP2 than control group (68.2+/−4.1% vs. 48.5+/−2.8%; $p<0.01$), while there was no significant difference between HHP1 and control group (49.0+/−2.6% vs. 48.5+/−2.8%; $p<0.05$). After the embryo transfer, one of the two sows was diagnosed as pregnant. Since there was no sign of labor at day 121 the farrowing was induced with an injection of prostaglandin, which resulted in delivery, and two healthy piglets were born naturally after a gestation length of 122 days.

TABLE 10

Developmental competence of SCNT porcine embryos derived from group of HHP1, HHP2, and Control

| Treatment groups | Number of reconstructed embryos | Total number of blastocysts | Mean blastocyst rate (%) |
| --- | --- | --- | --- |
| HHP1 | 90 | 45 | 49.0 ± 2.6[a] |
| HHP2 | 144 | 98 | 68.2 ± 4.1[b] |
| Control | 204 | 98 | 48.5 ± 2.8[a] |

Values with different superscript in the same column mean significant difference.

In Experiment 2, after vitrification and warming, survival rates of blastocysts derived from HHP2 oocytes were higher than those developed from control oocytes (61.6+/−4.0% vs. 30.2+/−3.9%; $p<0.01$) (Table 11). There was no significant difference in average cell numbers of blastocysts derived from either HHP2 treated or nontreated oocytes (56+/−4% vs. 49+/−5%; p □<0.05).

TABLE 11

Mean cell number and cryosurvival of porcine HMC embryos derived from group of HHP2 and Control

| Treatment groups | Number of reconstructed embryos | Mean cell number of blastocysts | Mean rate of reexpanded blastocysts after warming (%) |
|---|---|---|---|
| HHP2 | 87 | 56 ± 4$^a$ | 62 ± 4$^a$ |
| Control | 63 | 49 ± 5$^a$ | 30 ± 4$^b$ |

Values with different superscript in the same column mean significant difference.

Example 11

Improved Embryoid Body Cryopreservation and Cardiomyocyte Differentiation Following High Hydrostatic Pressure Treatment Materials and methods: Mouse ESCs with 129/SvJ origin were harvested with 0.05% Trypsin-EDTA and the dissociated cells were suspended in medium without LIF and hanging drops (HD) containing 800 cells were created. EBs were allowed to form for 2 days in HDs before culture in suspension for the next 2 days. On day 4 the EBs were assigned to four experimental groups (HHP treated/not treated, with or without vitrification) and 4 repetitions were made. Treatment was performed at 600 bar for 30 min at 24° C. in a computer controlled pressurizing device (Cryo-Innovation Inc. Budapest, Hungary). After pressure treatment the EBs were/or not vitrified and warmed by solid surface vitrification method (SSV; Dinnyes et al., 2000), than the EBs were individually placed onto gelatin coated dishes. The survival rate were determined by observing the attached EBs. The capability of differentiation into cardiomyocytes were defined by microscopic observation of the beeting EBs and cardiomyocyte specific IHC staining.

Results: Studies showed that the pressure treatment highly improved the efficiency of in vitro differentiation towards cardiac lineages (74.6% vs. 36.9%, respectively).

In conclusion SSV combined with HHP is a highly suitable method to cryopreserve EBs and to improve the efficacy of cardiac differentiation from cryopreserved samples.

REFERENCES

Abe, F., and Horikoshi, K. (1995). Hydrostatic pressure promotes the acidification of vacuoles in *Saccharomyces cerevisiae*. FEMS Microbiol Lett 130, 307-312.

Abe, F., and Horikoshi, K. (1997). Vacuolar acidification in *Saccharomyces cerevisiae* induced by elevated hydrostatic pressure is transient and is mediated by vacuolar H+-ATPase. Extremophiles 1, 89-93.

Abe, F., and Horikoshi, K. (1998). Analysis of intracellular pH in the yeast *Saccharomyces cerevisiae* under elevated hydrostatic pressure: a study in baro-(piezo-) physiology. Extremophiles 2, 223-228.

Abe, F., Kato, C., and Horikoshi, K. (1999). Pressure-regulated metabolism in microorganisms. Trends Microbiol 7, 447-453.

Aldridge, B. E., Bruner, L. J. (1985). Pressure effects on mechanisms of charge transport across bilayer membranes. Biochim Biophys Acta 817, 343-354.

Archer, J., Gook, D. A., Edgar, D. H. (2003). Blastocyst formation and cell numbers in human frozen-thawed embryos following extended culture. Human Reproduction (Oxford, England) 18, 1669-1673.

Baguisi, A., Arav, A., Crosby, T. F., Roche, J. F., and Boland, M. P. (1987). Hypothermic storage of sheep embryos with antifreeze proteins: development in vitro and in vivo. Theriogenology 48, 1017-1024.

Bridgeman, P. E. (1970). The physics of high pressure. New York: Dover

Bridgman, P. W. (1911). Water in the liquid and five solid forms under pressure. Proceedings of the American Academy of Arts and Science 47, 441-558.

Butz P, Ludwig H. (1986). Pressure inactivation of microorganisms at moderate temperatures. Physica B+C 139-140, 875-877.

Dinnyés A, Dai Y, Jiang S, et al. High developmental rates of vitrified bovine oocytes following par-thenogenetic activation, in vitro fertilization, and somatic cell nuclear transfer. Biol Reprod 2000; 63: 513-18.

Dinnyes A, Polgar Z, Pribenszky C, Pirity M K. Improved embryoid body cryopreservation and cardiomyocyte differentiation following high hydrostatic pressure treatment. Proceedings of The 1st International Congress on Controversies in Cryopreservation of Stem Cells, Reproductive Cells, Tissue and Organs, Valencia, Spain (CometMed, Israel), 2010; A-7.

Du Y, Lin L, Schmidt M, Bøgh IB, Kragh P M, Sørensen CB, Li J, Pump S, Pribenszky C, Molnár M, Kuwayama M, Zhang X, et al. High hydrostatic pressure treatment of porcine oocytes before handmade cloning improves developmental competence and cryosurvival. Cloning Stem Cells 2008; 10:325-330.

Du Y, Pribenszky C, Molnár M, Zhang X, Yang H, Kuwayama M, Pedersen A M, Villemoes K, Bolund L, Vajta G. High hydrostatic pressure: a new way to improve in vitro developmental competence of porcine matured oocytes after vitrification. Reproduction 2008; 135:13-17.

Fahy, G. M., MacFarane, D. R., Angell, C. A. and Meryman, H. T. (1984). Vitrification as an approach to cryopreservation. Cryobiology 21. 407-426.

Fukuda, A., Osawa, T., Oda, H., Tanaka, T., Toyokuni, S, and Uchida, K. Oxidative stress response in iron induced acute nephrotoxicity: enhanced expression of heat shock protein 90. Biochem Biophys Res Commun 1996; 219:76-81.

Garcia-Gardena, G., Fan, R., Shah, V., Sorrentino, R., Cirino, G., Papapetropoulos. Dynamic activation of endothelialnitric oxide synthase by HSP90. Nature 1998; 392: 821-4.

Graumann, P. L., Marahiel M. A. (1999). Cold shock proteins CspB and CspC are major stationary-phase-induced proteins in *Bacillus subtilis*. Arch Microbiol 171, 135-138.

Gross, M., Jaenicke, R. (1994). Proteins under pressure. The influence of high hydrostatic pressure on structure, function and assembly of proteins and protein complexes. Eur J Biochem 221, 617-630.

Huang, S. Y., Kuo, Y. H., Lee, W. C., Tsou, H. L., Lee, Y. P., Chang, H. L. et al. Substantial decrease of heat-shock protein 90 precedes the decline of sperm motility during cooling of boar spermatozoa. Theriogenology 1999; 51:1007-16.

Huang, S. Y., Kuo, Y. H., Tsou, H. L., Lee, W. C., King, Y. T., Huang, H. C. et al. The decline of porcine sperm motility by geldanamycin, a specific inhibitor of heat shock protein 90 (HSP90). Theriogenology 2000; 53:1117-84.

Ishwar, A. K., Memon, M. A. (1996). Embryo transfer in sheep and goats: a review Small Ruminant Research 19, 35-43.

Jaenicke, R. (1991). Protein stability and molecular adaptation to extreme conditions. Eur J Biochem 202, 715-728.

Kuwayama, M., Vajta, G., Kato, 0., et al. (2005). Highly efficient vitrification method for cryopreservation of human oocytes. Reprod. Biomed. Online 11, 300-308.

LaTena, A., Brandi, A., Falconi, M., Spurio, R., Pon, C. L., Gualerzi, C. O. (1991). Identification of a cold-shock transcriptional enhancer of the *Escherichia coli* major cold shock gene encoding nucleotide protein H-NS. Proc Natl Acad Sci USA 88, 10907-10911.

Leibo, S. P. and Songsasen, N. (2002). Cryopreservation of gamets and embryos of non-domestic species. Theriogenology 57. 303-326.

Lin L, Pribenszky C, MolnAr M, Kragh P M, Du Y, Zhang X, Yang H, Bolund L, Callesen H, Macháty Z, Vajta G. High hydrostatic pressure treatment of porcine oocytes induces parthenogenetic activation. Cell Reprog 2010; 12:475-480.

Macdonald, A. G. (1987). The role of membrane fluidity in complex processes under high pressure. In: Jonnasch, H. W., Marquis, R. E., Zimmerman, A. M., editors. Current Perspectives in High Pressure Biology. London: Academic Press pp. 207-223.

Medeiro, C. M. O., Forell, F., Oliveira, A. T. D., and Rodrigues, 2002. J. L. Current Status Of Sperm Cryopreservation: Why Isn't It Better? Theriogenology 57:327-344.

Murakami, T. H., Zimmerman, A. M. (1973). DNA syntheseis in Tetrahymena: a pressure study. Cytobios 7, 171-181.

Nowshari, M. A., Brem, G. (1998). Effect of cryoprotectants and their concentration on post-thaw survival and development of expanded mouse blastocysts frozen by a simple rapid-freezing procedure. Theriogenology 50, 1001-1013.

Palou, E., Lopez-Malo, A., Barbosa-Canovas, G. V., Welti-Chanes, J., and Swanson, B. G. (1997). Kinetic analysis of *Zygosaccharomyces bailii* inactivation by high hydrostatic pressure. Lebensm.-Wiss. U. Technol. 30, 703-708.

Pearl, L. H. and Prodromou, C. Structure and in vivo function of Hsp 90. Curr. Opin Struct Biol 2000; 10:46-51.

Péqueux, A., and Gilles, R. (1978). Effects of high hydrostatic pressures on the activity of the membrane ATPases of some organs implicated in hydromineral regulation. Comp Biochem Physiol B Biochem Mol Biol 59, 207-212.

Phadtare S., Alasina J. and Inouye M. (1999). Cold-shock response and cold-shock proteins. Curr Opin Microbiol 2, 175-180 Graumann, P. L. and Marahiel, M. A. (1999). Cold shock proteins CspB and CspC are major stationary-phase-induced proteins in *Bacillus subtilis*. Arch Microbiol 171. 135-138.

Phadtare, S., Alasina, J., Inouye, M. (1999). Cold-shock response and cold-shock proteins. Curr Opin Microbiol 2, 175-180.

Pribenszky C, Du Y, Molnár M, Harnos A, Vajta G. Increased stress tolerance of pig oocytes after high hydrostatic pressure treatment. Anim Reprod Sci 2008; 106:200-207.

Pribenszky C, Du Y, Molnar M, Vajta G. Sublethal stress on porcine oocytes enhances the efficacy of ART procedures. Human Reprod 2008; 23:161.

Pribenszky C, Mátyás S, Losonczi E, Stanca C, Bock I, Vajta G. Stress for stress tolerance: Improving cell survival by sublethal stress treatment of eggs before vitrification pilot study. Fertil Steril (Scientific Abstracts from the 2010 Annual Meeting of the American Society for Reproductive Medicine) 2010; 94:0-106.

Pribenszky C, Molnár M, Cseh S, Solti L. Improving post-thaw survival of cryopreserved mouse blastocysts by hydrostatic pressure challenge. Anim Reprod Sci 2005; 87:143-150.

Prodromou, C., Roe, S. M., O'Brian, R., Ladbury, J. E., Piper, P. W. amd Pearl, L. H. Identification and structural characterization of the ATP/ADP-binding site in the HSP90 molecular chaperone. Cell 1997; 90:65-75.

Rall, W. F., and Fahy, G. M. (1985). Ice-free cryopreservation of mouse embryos at $-196°$ C. by vitrification. Nature 313, 573-575.

Reubinoff, B. E., Pera, M. F., Vajta, G., and Trounson, A. O. (2001). Effective cryopreservation of human embryonic stem cells by the open pulled straw vitrification method. Human Reproduction 16, 2187-2194.

Routray, P., Suzuki, T., Strüssmann, C. A. and Takai, R. (2002). Factors affecting the uptake of DMSO by the eggs and embryos of medaka, *Oryzias latipes*. Theriogenology 58. 1483-1496.

Schmid, G., Lüdemann, H. D., and Jaenicke, R. (1975) High pressure effects on the activity of glycolytic enzymes. Biophys Chem 3, 90-98.

Schuster, B., Sleytr, U. B. (2002). The effect of hydrostatic pressure on S-layer-supported lipid membranes. Biochim Biophys Acta 1563, 29-34.

Seki, K., Toyoshima, M. (1998). Preserving tardigrades under pressure. Nature 395, 853-854.

Silva, J. L., Foguel, D., Royer, C. A. (2001). Pressure provides new insights into protein folding, dynamics and structure. Trends Biochem Sci 26, 612-618.

Spilimbergo, S., Elvassore, N., Bertucco, A. (2002). Microbial inactivation by high-pressure. The Journal of Supercritical Fluids 22, 55-63.

Stachecki, J, J., Cohen, J., Schimmel, T., Willadsen, S. M. (2002). Fetal development of mouse oocytes and zygotes cryopreserved in a nonconventional freezing medium. Cryobiology 44, 5-13.

Vajta, G., Bartels, P., Joubert, J., et al. (2004). Production of a healthy calf by somatic cell nuclear transfer without micro-manipulators and carbon dioxide incubators using the Handmade Cloning (HMC) and the Submarine Incubation System (SIS). Theriogenology 62, 1465-1472.

Van Wagtendonk-De Leeuw, A. M., Den Daas, J. H., Kruip, T. A., Rall, W. F. (1995). Comparison of the efficacy of conventional slow freezing and rapid cryopreservation methods for bovine embryos. Cryobiology 32, 157-167.

Van Wagtendonk-De Leeuw, A. M., Den Haas, J. H. G., and Rall, W. F. 1997. Field trials to compare pregnancy rates of bovine embryo cryopreservation methods: vitrification and one-step dilution versus slow freezing and three-step dilution. Theriogenology 48, 1071-1084.

Watson, P. F. The effect of cold shock on sperm cell membranes. In: Morris, G. J. and Clarke, A. eds. Effects of low temperature on biological membranes. London: Academic Press; 1981. p. 189-218.

Weber, G., Drickamer, H. G. (1983). The effect of high pressure upon proteins and other biomolecules. Q Rev Biophys 16, 89-112.

Welch, T. J., Farewell, A., Neidhardt, F. C., Bartlett, D. H. (1993). Stress response of *Escherichia coli* to elevated hydrostatic pressure. J Bacteriol 175, 7170-7177.

Wemekamp-Kamphuis, H. H., Karatzas, A. K., Wouters, J. A., Abee, T. (2002). Enhanced levels of cold shock proteins in *Listeria monocytogenes* LO28 upon exposure to low temperature and high hydrostatic pressure. Appl Environ Microbiol 68, 456-63.

Wen-Lei C A O et al. Cryopreservation-induced decrease in heat-shock protein 90 in human spermatozoa and its mechanism. Asian J Androl 2003; 5:43-46.

Wouters, J. A., Jeynov, B., Rombouts, F. M., de Vos, W. M., Kuipers, O. P., Abee, T. (1999). Analysis of the role of 7 kDa cold-shock proteins of *Lactobacillus lactis* MG1363 in cryoprotection. Microbiology 145, 3185-3194.

Yager, P., Chang, E. L. (1983). Destabilization of a lipid non-bilayer phase by high pressure. Biochim Biophys Acta 731, 491-494.

Yamanaka, K., Fang, L., Inouye, M. (1998). The CspA family in *Escherichia coli*: multiple gene duplication for stress adaptation. Mol Microbiol 27, 247-255.

Yoshioka, K., Suzuki, C., Tanaka, A., et al. (2002). Birth of piglets derived from porcine zygotes cultured in a chemically defined medium. Biol. Reprod. 66, 112-119.

The invention claimed is:

1. A method for improving post-thaw survival of cryopreserved viable biological material comprising
    (a) applying hydrostatic pressure in the range of 10 to 200 MPa to said viable biological material, optionally according to a predetermined pressure-time profile;
    (b) keeping the said viable biological material at the hydrostatic pressure for a predetermined time period;
    (c) releasing the hydrostatic pressure;
    (d) further cryopreserving the said viable biological material using any protocol applicable thereto,
wherein said biological material is selected from the group consisting of oocytes, sperms, zygotes, morulas, blastocysts, embryos, stem cells and cells of a vertebrate animal.

2. The method according to claim 1 wherein the said hydrostatic pressure is applied for a time period between 1 second and 300 minutes.

3. The method according to claim 2 wherein the said hydrostatic pressure is applied for a time period between 1 second and 150 minutes.

4. The method according to claim 2 wherein the said hydrostatic pressure is applied for a time period between 1 second and 90 minutes.

5. The method according to claim 2 wherein the said hydrostatic pressure is applied for a time period between 1 second and 60 minutes.

6. The method according to claim 1 wherein the pressure is released gradually over a time period between 1 second and 4 hours.

7. The method according to claim 1 wherein the said vertebrate animal is a fish, a bird or a mammal.

8. The method according to claim 7 wherein said vertebrae animal is selected from the group consisting of bovine, equine, caprine, ovine, swine, other livestocks, pets, and primates, including humans.

9. The method according to claim 1 wherein the said hydrostatic pressure is in the range of 10 to 100 MPa.

10. The method according to claim 1 wherein the said hydrostatic pressure is in the range of 30 to 60 MPa.

11. The method according to claim 1 wherein the time period is selected based on the pressure tolerance of the viable biological material.

12. The method according to claim 1, further comprising before step (a), placing the biological material into a pressurizing device which includes a pressure chamber suitable for receiving the biological material, and means to provide controlled pressure in the range of 10 to 200 MPa.

13. The method according to claim 12, wherein the pressurizing device comprises means to maintain the pressure for a time period between 1 second and 300 minutes.

14. The method according to claim 12, wherein a control system is provided for controlling the depressurization of the pressure chamber over a period between 1 second and 4 hours.

15. The method according to claim 1 wherein said biological material is oocytes.

16. The method according to claim 1 wherein said biological material is stem cells.

17. A method for improving post-thaw survival of cryopreserved viable biological material comprising
    (a) applying hydrostatic pressure in the range of 10 to 75 MPa 40 MPa to said viable biological material, optionally according to a predetermined pressure-time profile;
    (b) keeping the said viable biological material at the hydrostatic pressure for a predetermined time period;
    (c) releasing the hydrostatic pressure;
    (d) further cryopreserving the said viable biological material using any protocol applicable thereto.

18. The method according to claim 17 wherein said biological material is selected from the group consisting of oocytes, sperms, zygotes, morulas, blastocysts, embryos, stem cells, cells, tissues and organs of a vertebrate animal.

* * * * *

UNITED STATES PATENT AND TRADEMARK OFFICE
CERTIFICATE OF CORRECTION

PATENT NO. : 8,415,093 B2  
APPLICATION NO. : 13/016512  
DATED : April 9, 2013  
INVENTOR(S) : Pribenszky et al.

Page 1 of 1

It is certified that error appears in the above-identified patent and that said Letters Patent is hereby corrected as shown below:

In the Claims:

At column 34, in Claim 17, lines 30-31, "10 to 75 MPa 40 MPa" should read -- 10 to 40 MPa --.

Signed and Sealed this
Twenty-eighth Day of May, 2013

Teresa Stanek Rea
*Acting Director of the United States Patent and Trademark Office*